(12) United States Patent
Donaldson et al.

(10) Patent No.: US 7,994,292 B2
(45) Date of Patent: Aug. 9, 2011

(54) MU-1, MEMBER OF THE CYTOKINE RECEPTOR FAMILY

(75) Inventors: Debra D. Donaldson, Burlingame, CA (US); Michelle J. Unger, Jersey City, NJ (US)

(73) Assignee: Genetics Institute, LLC, Madison, NJ (US)

( * ) Notice: Subject to any disclaimer, the term of this patent is extended or adjusted under 35 U.S.C. 154(b) by 0 days.

(21) Appl. No.: 12/695,485

(22) Filed: Jan. 28, 2010

(65) Prior Publication Data

US 2010/0130729 A1    May 27, 2010

Related U.S. Application Data

(60) Division of application No. 11/957,891, filed on Dec. 17, 2007, now Pat. No. 7,705,123, which is a continuation of application No. 09/569,384, filed on May 11, 2000, now abandoned, which is a continuation-in-part of application No. 09/560,766, filed on Apr. 28, 2000, now abandoned, which is a continuation of application No. 09/040,005, filed on Mar. 17, 1998, now Pat. No. 6,057,128.

(51) Int. Cl.
*C07K 16/28* (2006.01)
*C07K 14/705* (2006.01)
(52) U.S. Cl. ................... 530/388.22; 424/172.1
(58) Field of Classification Search .................. None
See application file for complete search history.

(56) References Cited

U.S. PATENT DOCUMENTS

| | | | |
|---|---|---|---|
| 5,011,912 A * | 4/1991 | Hopp et al. | 530/387.9 |
| 5,098,833 A | 3/1992 | Lasky et al. | 435/69.1 |
| 5,116,964 A | 5/1992 | Capon et al. | 536/27 |
| 5,155,027 A | 10/1992 | Sledziewski et al. | 435/69.7 |
| 5,216,131 A | 6/1993 | Lasky et al. | 530/350 |
| 5,225,538 A | 7/1993 | Capon et al. | 530/387.3 |
| 5,428,130 A | 6/1995 | Capon et al. | 530/350 |
| 5,447,851 A | 9/1995 | Beutler et al. | 435/69.7 |
| 5,455,165 A | 10/1995 | Capon et al. | 435/64.7 |
| 5,514,582 A | 5/1996 | Capon et al. | 435/252.3 |
| 5,567,584 A | 10/1996 | Sledziewski et al. | 435/6 |
| 5,714,147 A | 2/1998 | Capon et al. | 424/178.1 |
| 5,750,375 A | 5/1998 | Sledziewski et al. | 435/69.7 |
| 5,840,844 A | 11/1998 | Lasky et al. | 530/350 |
| 5,843,725 A | 12/1998 | Sledziewski et al. | 435/69.7 |
| 6,018,026 A | 1/2000 | Sledziewski et al. | 530/350 |
| 6,057,128 A | 5/2000 | Donaldson et al. | 435/69.1 |
| 6,136,310 A | 10/2000 | Hanna et al. | 424/154.1 |
| 6,291,212 B1 | 9/2001 | Sledziewski et al. | 435/69.1 |
| 6,291,646 B1 | 9/2001 | Sledziewski et al. | 530/350 |
| 6,300,099 B1 | 10/2001 | Sledziewski et al. | 435/69.1 |
| 6,307,024 B1 | 10/2001 | Novak et al. | 530/351 |
| 6,323,323 B1 | 11/2001 | Sledziewski et al. | 530/387.3 |
| 6,406,697 B1 | 6/2002 | Capon et al. | 424/178.1 |
| 6,576,744 B1 | 6/2003 | Presnell et al. | 530/351 |
| 6,605,272 B2 | 8/2003 | Novak et al. | 424/85.2 |
| 6,686,178 B2 | 2/2004 | Novak et al. | 435/69.52 |
| 6,692,924 B2 | 2/2004 | Presnell et al. | 435/7.1 |
| 6,777,539 B2 | 8/2004 | Sprecher et al. | 530/350 |
| 6,803,451 B2 | 10/2004 | Presnell | 530/351 |
| 7,189,400 B2 | 3/2007 | Carter et al. | 424/185.1 |
| 7,198,789 B2 | 4/2007 | Carter et al. | 424/130.1 |
| 7,314,623 B2 | 1/2008 | Grusby et al. | 424/185.1 |
| 7,495,085 B2 | 2/2009 | Valge-Archer et al. | 530/387.9 |
| 2001/0025022 A1 | 9/2001 | Kikly et al. | 514/2 |
| 2002/0090680 A1 | 7/2002 | Hodge | 435/69.1 |
| 2002/0128446 A1 | 9/2002 | Novak et al. | 530/351 |
| 2002/0137677 A1 | 9/2002 | Sprecher et al. | 514/12 |
| 2002/0160451 A1 | 10/2002 | Masiakowski et al. | 435/69.1 |
| 2003/0134390 A1 | 7/2003 | Presnell et al. | 435/69.52 |
| 2003/0148447 A1 | 8/2003 | Presnell et al. | 435/69.1 |
| 2004/0016010 A1 | 1/2004 | Kasaian et al. | 800/18 |
| 2004/0235743 A1 | 11/2004 | Sprecher et al. | 514/12 |
| 2006/0024268 A1 | 2/2006 | Kasaian et al. | 424/85.2 |
| 2006/0039902 A1 | 2/2006 | Young et al. | 424/133.1 |
| 2006/0159655 A1 | 7/2006 | Collins et al. | 424/85.2 |
| 2006/0257403 A1 | 11/2006 | Young et al. | 424/144.1 |
| 2008/0241098 A1 | 10/2008 | Young et al. | 424/85.2 |
| 2009/0197803 A1 | 8/2009 | Grusby et al. | 514/12 |
| 2009/0298081 A1 | 12/2009 | Bloom et al. | 435/6 |
| 2009/0298167 A1 | 12/2009 | Bloom et al. | 435/348 |

FOREIGN PATENT DOCUMENTS

| | | |
|---|---|---|
| EP | 0 812 913 | 12/1997 |
| EP | 1 088 831 | 4/2001 |
| WO | WO 96/04388 | 2/1996 |
| WO | WO 97/20926 | 6/1997 |
| WO | WO 97/31946 | 9/1997 |
| WO | WO 97/33913 | 9/1997 |
| WO | WO 97/47741 | 12/1997 |
| WO | WO 97/47742 | 12/1997 |
| WO | WO 98/10638 | 3/1998 |
| WO | WO 98/11225 | 3/1998 |
| WO | WO 98/31811 | 7/1998 |
| WO | WO 99/47675 | 9/1999 |
| WO | WO 99/67290 | 12/1999 |
| WO | WO 00/08152 | 2/2000 |
| WO | WO 00/17235 | 3/2000 |
| WO | WO 00/27882 | 5/2000 |

(Continued)

OTHER PUBLICATIONS

Cosman "The Hematopoietin Receptor Superfamily", *Cytokine*, vol. 5, No. 2, Mar. 1993, pp. 95-106.
Gonda and D'Andrea "Activating Mutations in Cytokine Receptors: Implications for Receptor Function and Role in Disease", *Blood*, vol. 89, No. 2, Jan. 1997, pp. 355-369.
Goldsmith et al. "The Cytoplasmic Domain of the Interleukin-2 Receptor β Chain Contains Both Unique and Functionally Redundant Signal Transduction Elements", *J. Biol. Chem.*, vol. 269, 1994, pp. 14698-14704.

(Continued)

*Primary Examiner* — John Ulm

(57) ABSTRACT

Polynucleotides encoding the MU-1 hematopoietin receptor superfamily chain and fragments thereof are disclosed. MU-1 proteins, antibodies (and fragments thereof) that specifically bind to MU-1 proteins (and fragments thereof), and methods for their production are also disclosed.

13 Claims, 10 Drawing Sheets

FOREIGN PATENT DOCUMENTS

| | | |
|---|---|---|
| WO | WO 00/53761 | 9/2000 |
| WO | WO 00/69880 | 11/2000 |
| WO | WO 01/36467 | 5/2001 |
| WO | WO 01/46261 | 6/2001 |
| WO | WO 01/77171 | 10/2001 |
| WO | WO 01/85792 | 11/2001 |
| WO | WO 03/040313 | 3/2003 |
| WO | WO 03/028630 | 4/2003 |
| WO | WO 2004/007682 | 1/2004 |
| WO | WO 2004/083249 | 9/2004 |
| WO | WO 2004/084835 | 10/2004 |
| WO | WO 2005/112983 | 12/2005 |
| WO | WO 2006/113331 | 10/2006 |
| WO | WO 2006/135385 | 12/2006 |
| WO | WO 2009/100035 | 8/2009 |

OTHER PUBLICATIONS

Goldsmith et al. "Growth Signal Transduction by the Human Interleukin-2 Receptor Requires Cytoplasmic Tyrosines of the β Chain and Non-tyrosine Residues of the γc Chain", *J. Biol. Chem.*, vol. 270, 1995, pp. 21729-21737.

Altschul et al. "Gapped BLAST and PSI-BLAST: a new generation of protein database search programs", *Nuc. Acids Res.*, vol. 25, No. 17, 1997, pp. 3389-3402.

Frishman et al. "The PEDANT genome database", *Nuc. Acids Res.*, vol. 31, No. 1, 2003, pp. 207-211.

Brenner et al. "Assessing sequence comparison methods with reliable structurally identified distant evolutionary relationships", *Proc. Natl. Acad. Sci. USA*, vol. 95, May 1998, pp. 6073-6078.

Brenner et al. "The ASTRAL compendium for protein structure and sequence analysis", *Nuc. Acids Res.*, vol. 28, No. 1, 2000, pp. 254-56.

Sander and Schneider "Database of Homology-Derived Protein Structures and the Structural Meaning of Sequence Alignment", *Proteins*, vol. 9, 1991, pp. 56-68.

Chung and Subbiah "A structural explanation for the twilight zone of protein sequence homology", *Structure (London)*, vol. 4, 1996, pp. 1123-1127.

Fitch "An Improved Method of Testing for Evolutionary Homology", *J. Mol. Biol.*, vol. 16, 1966, pp. 9-16.

Bagley et al. "The Structural and Functional Basis of Cytokine Receptor Activation: Lessons From the Common β Subunit of the Granulocyte-Macrophage Colony-Stimulating Factor, Interleukin-3 (IL-3), and IL-5 Receptors", *Blood*, vol. 89, No. 5, Mar. 1, 1997, pp. 1471-1482.

Yamasaki et al. "Cloning and Expression of the Human Interleukin-6 (BSF-2/IFNβ 2) Receptor", *Science*, vol. 241, Aug. 12, 1988, pp. 825-828.

Somers et al. "1.9 Å crystal structure of interleukin 6: implications for a novel mode of receptor dimerization and signaling", *EMBO J.*, vol. 16, No. 5, 1997, p. 989-97.

Taga and Kishimoto "Cytokine receptors and signal transduction", *FASEB J.*, vol. 6, 1992, pp. 3387-3396.

Minami et al. "The IL-2 Receptor Complex: Its Structure, Function, and Target Genes", *Annu. Rev. Immunol.*, vol. 11, 1993, pp. 245-267.

DiSanto "Cytokines: Shared receptors, distinct functions", Curr. Biol., vol. 7, 1997, pp. R424-R426.

Vita et al. "Characterization and Comparison of the Interleukin 13 Receptor with the Interleukin 4 Receptor on Several Cell Types", *J. Biol. Chem.*, vol. 270, No. 8, 1995, pp. 3512-3517.

Uckun et al. "Interleukin 7 receptor ligation stimulates tyrosine phosphorylation, inositol phospholipid turnover, and clonal proliferation of human B-cell precursors", *Proc. Natl. Acad. Sci. USA*, vol. 88, May 1991, pp. 3589-3593.

Demoulin et al. "A Single Tyrosine of the Interleukin-9 (IL-9) Receptor is Required for STAT Activation, Antiapoptotic Activity, and Growth Regulation by IL-9", *Mol. Cell. Biol.*, vol. 16, No. 9, Sep. 1996, pp. 4710-4716.

Leonard and Spolski "Interleukin-21: A Modulator of Lymphoid Proliferation, Apoptosis and Differentiation", Nat. Rev. Immunol., vol. 5, Sep. 2005, pp. 688-698.

Murakami "Critical cytoplasmic region of the interleukin 6 signal transducer gp130 is conserved in the cytokine receptor family", *Proc. Natl. Acad. Sci. USA*, vol. 88, Dec. 1991, pp. 11349-11353.

Maliszewski and Fanslow "Soluble receptors for IL-1 and IL-4: biological activity and therapeutic potential", *Trends Biotech.*, vol. 8, 1990, pp. 324-329.

Hou et al. "Identification and Purification of Human Stat Proteins Activated in Response to Interleukin-2", *Immunity*, vol. 2, 1995, pp. 321-329.

Pericle et al. "Immunocompromised Tumor-Bearing Mice Show a Selective Loss of STAT5a/b Expression in T and B Lymphocytes", J. Immunol., vol. 159, 1997, pp. 2580-2585.

Pericle et al. "Cutting Edge: HIV-1 Infection Induces a Selective Reduction in STAT5 Protein Expression", *J. Immunol.*, vol. 160, 1998, pp. 28-31.

Chrétien et al. "Erythropoietin-induced erythroid differentiation of the human erythroleukemia cell line TF-1 correlates with impaired STAT5 activation", *EMBO J.*, vol. 15, No. 16, 1996, pp. 4174-4181.

Nakajima et al., "An Indirect Effect of Stat5a in IL-2-Induced Proliferation: A Critical Role for Stat5a in IL-2-Mediated IL-2 Receptor α Chain Induction", *Immunity*, vol. 7, 1997, pp. 691-701.

Bazan "Structural design and molecular evolution of a cytokine receptor superfamily," *Proc. Natl. Acad. Sci. USA* 87:6934-38 (1990).

Imler et al. "Identification of three adjacent amino acids of interleukin-2 receptor β chain which control the affinity and the specificity of the interaction with interleukin-2," *EMBO J.* 11:2047-53 (1992).

LaRosa et al. "Amino Terminus of the Interleukin-8 Receptor is a Major Determinant of Receptor Subtype Specificity," *J. Biol. Chem.* 267:25402-06 (1992).

Schimmenti et al. "Localization of an essential ligand binding determinant of the human erythropoietin receptor to a domain N-terminal to the WSXWS motif: implications for soluble receptor function," *Exp. Hematol.* 23:1341-46 (1995).

Mulhern et al. "The Solution Structure of the Cytokine-binding Domain of the Common β-Chain of the Receptors for Granulocyte-Macrophage Colony-stimulating Factor, Interleukin-3 and Interleukin-5," *J. Mol. Biol.* 297:989-1001 (2000).

Woodcock et al. "Three residues in the common β chain of the human GM-CSF, IL-3 and IL-5 receptors are essential for GM-CSF and IL-5 but not IL-3 high affinity binding and interact with Glu21 of GM-CSF," *EMBO J.* 13:5176-85 (1994).

D'Andrea et al., "Expression cloning of the murine erythropoietin receptor," *Cell*, 57:277-285 (1989).

Hatakeyama et al., "Interleukin-2 receptor beta chain gene: Generation of three receptor forms by cloned human alpha and beta chain cDNA's," *Science*, 244:551-556 (1989).

Yan et al., "Two-Amino Acid Molecular Switch in an Epithelial Morphogen That Regulates Binding to Two Distinct Receptors," *Science*, 290:523-527 (2000).

Parrish-Novak et al., "Interleukin 21 and its receptor are involved in NK cell expansion and regulation of lymphocyte function," *Nature*, 408:57-63 (2000).

Ozaki et al., "Cloning of a type I cytokine receptor most related to the IL-2 receptor β chain," *Proc. Natl. Acad. Sci. USA*, 97(21):11439-11444 (2000).

EMBL Database Accession No. AC002303 (Jun. 26, 1997).

O'Dowd et al., "Cloning and chromosomal mapping of four putative novel human G-protein-coupled receptor genes," *Gene* 187(1):75-81, (1997).

Database EMBL. ID HS795114, Accession No. R52795, May 25, 1995.

Caput, D. et al., "Cloning and characterization of a specific interleukin (IL)-13 binding protein structurally related to the IL-5 receptor a chain," *The Journal of Biological Chemistry*, 271(28):16921-16926, (1996).

Birö et al., "The effects of wsews pentapeptide and wsews-specific monoclonal antibodies on constitutive and 11-6 induced acute phase," *Immunology Letters*, 46:183-187, (1995).

Zhang et al., "Identification, purification, and characterization of a soluble interleukin (IL)-13 binding protein," *Journal of Biological Chemistry*, 272(14):9474-9480, (1997).

Debinski, W. et al., "A novel chimeric protein composed of interleukin-13 and pseudomonas exotoxin is highly cytotoxic to human carcinoma cells expressing receptors for interleukin-4," *Journal of Biological Chemistry*, 270(28):16775-16780, (1995).

Page, L.A. et al., "An aniproliferative bioassay for interleukin-4," Journal of Immunological Methods, 189(1): 129-135, (1996).

Lai Chun-Fai et al., "STAT3 and STAT5B are targets of two different signal pathways activated by hematopoietin receptors and control transcription via separate cytokine response elements," Journal of Biological Chemistry, 270(4):23254-23257, (1995).

Database EMBL, Accession No. AF279436, Jul. 18, 2000.

Database EMBL, Accession No. AB049137, Sep. 23, 2000.

GenBank Accession No. M26062, Human interleukin 2 receptor beta chain (p70-75) mRNA, complete cds (1995), printed Apr. 14, 2009, 4 pages.

Dusanter-Fourt et al. "Transduction du signal par les recepteurs de cytokines" *Medecine/Sciences* 10:825-35 (1994), 12 pages (with English Abstract).

GenBank Accession No. AAA59143.1, Interleukin 2 receptor beta chain precursor peptide (1995), printed Apr. 14, 2009, 2 pages.

Kirken et al., "Mechanisms of Cytokine Signal Transduction: IL-2, IL-4 and Prolactin as Hematopoietin Receptor Models,"Veterinary Immunology and Immunopathology 63(1-2):27-36 (May 15, 1998).

* cited by examiner

| | | | | | |
|---|---|---|---|---|---|
| 1 | GTCGACGCGG | CGGTACCAGC | TGTCTGCCCA | CTTCTCCTGT | GGTGTGCCTC |
| 51 | ACGGTCACTT | GCTTGTCTGA | CCGCAAGTCT | GCCCATCCCT | GGGGCAGCCA |
| 101 | ACTGGCCTCA | GCCCGTGCCC | CAGGCGTGCC | CTGTCTCTGT | CTGGCTGCCC |
| 151 | CAGCCCTACT | GTCTTCCTCT | GTGTAGGCTC | TGCCCAGATG | CCCGGCTGGT |
| 201 | CCTCAGCCTC | AGGACTATCT | CAGCAGTGAC | TCCCCTGATT | CTGGACTTGC |
| 251 | ACCTGACTGA | ACTCCTGCCC | ACCTCAAACC | TTCACCTCCC | ACCACCACCA |
| 301 | CTCCGAGTCC | CGCTGTGACT | CCCACGCCCA | GGAGACCACC | CAAGTGCCCC |
| 351 | AGCCTAAAGA | ATGGCTTTCT | GAGAAAGACC | CTGAAGGAGT | AGGTCTGGGA |
| 401 | CACAGCATGC | CCCGGGGCCC | AGTGGCTGCC | TTACTCCTGC | TGATTCTCCA |
| 451 | TGGAGCTTGG | AGCTGCCTGG | ACCTCACTTG | CTACACTGAC | TACCTCTGGA |
| 501 | CCATCACCTG | TGTCCTGGAG | ACACGGAGCC | CAACCCCAG | CATACTCAGT |
| 551 | CTCACCTGGC | AAGATGAATA | TGAGGAACTT | CAGGACCAAG | AGACCTTCTG |
| 601 | CAGCCTACAC | AGGTCTGGCC | ACAACACCAC | ACATATATGG | TACACGTGCC |
| 651 | ATATGCGCTT | GTCTCAATTC | CTGTCCGATG | AAGTTTTCAT | TGTCAATGTG |
| 701 | ACGGACCAGT | CTGGCAACAA | CTCCCAAGAG | TGTGGCAGCT | TTGTCCTGGC |
| 751 | TGAGAGCATC | AAACCAGCTC | CCCCCTTGAA | CGTGACTGTG | GCCTTCTCAG |
| 801 | GACGCTATGA | TATCTCCTGG | GACTCAGCTT | ATGACGAACC | CTCCAACTAC |
| 851 | GTGCTGAGGG | GCAAGCTACA | ATATGAGCTG | CAGTATCGGA | ACCTCAGAGA |
| 901 | CCCCTATGCT | GTGAGGCCGG | TGACCAAGCT | GATCTCAGTG | GACTCAAGAA |
| 951 | ACGTCTCTCT | TCTCCCTGAA | GAGTTCCACA | AAGATTCTAG | CTACCAGCTG |
| 1001 | CAGGTGCGGG | CAGCGCCTCA | GCCAGGCACT | TCATTCAGGG | GGACCTGGAG |
| 1051 | TGAGTGGAGT | GACCCCGTCA | TCTTTCAGAC | CCAGGCTGGG | GAGCCCGAGG |
| 1101 | CAGGCTGGGA | CCCTCACATG | CTGCTGCTCC | TGGCTGTCTT | GATCATTGTC |
| 1151 | CTGGTTTTCA | TGGGTCTGAA | GATCCACCTG | CCTTGGAGGC | TATGGAAAAA |
| 1201 | GATATGGGCA | CCAGTGCCCA | CCCCTGAGAG | TTTCTTCCAG | CCCCTGTACA |
| 1251 | GGGAGCACAG | CGGGAACTTC | AAGAAATGGG | TTAATACCCC | TTTCACGGCC |
| 1301 | TCCAGCATAG | AGTTGGTGCC | ACAGAGTTCC | ACAACAACAT | CAGCCTTACA |
| 1351 | TCTGTCATTG | TATCCAGCCA | AGGAGAAGAA | GTTCCCGGGG | CTGCCGGGTC |
| 1401 | TGGAAGAGCA | ACTGGAGTGT | GATGGAATGT | CTGAGCCTGG | TCACTGGTGC |

Fig. 1A

| | |
|---|---|
| 1451 | ATAATCCCCT TGGCAGCTGG CCAAGCGGTC TCAGCCTACA GTGAGGAGAG |
| 1501 | AGACCGGCCA TATGGTCTGG TGTCCATTGA CACAGTGACT GTGGGAGATG |
| 1551 | CAGAGGGCCT GTGTGTCTGG CCCTGTAGCT GTGAGGATGA TGGCTATCCA |
| 1601 | GCCATGAACC TGGATGCTGG CCGAGAGTCT GGCCCTAATT CAGAGGATCT |
| 1651 | GCTCTTGGTC ACAGACCCTG CTTTTCTGTC TTGCGGCTGT GTCTCAGGTA |
| 1701 | GTGGTCTCAG GCTTGGAGGC TCCCCAGGCA GCCTACTGGA CAGGTTGAGG |
| 1751 | CTGTCATTTG CAAAGGAAGG GGACTGGACA GCAGACCCAA CCTGGAGAAC |
| 1801 | TGGGTCCCCA GGAGGGGGCT CTGAGAGTGA AGCAGGTTCC CCCCCTGGTC |
| 1851 | TGGACATGGA CACATTTGAC AGTGGCTTTG CAGGTTCAGA CTGTGGCAGC |
| 1901 | CCCGTGGAGA CTGATGAAGG ACCCCCTCGA AGCTATCTCC GCCAGTGGGT |
| 1951 | GGTCAGGACC CCTCCACCTG TGGACAGTGG AGCCCAGAGC AGCTAGCATA |
| 2001 | TAATAACCAG CTATAGTGAG AAGAGGCCTC TGAGCCTGGC ATTTACAGTG |
| 2051 | TGAACATGTA GGGGTGTGTG TGTGTGTGTG TGTGTGTGTG TGTGTGTGTG |
| 2101 | TGTGTGTGTG TGTGTGTGTG TGTCTTGGGT TGTGTGTTAG CACATCCATG |
| 2151 | TTGGGATTTG GTCTGTTGCT ATGTATTGTA ATGCTAAATT CTCTACCCAA |
| 2201 | AGTTCTAGGC CTACGAGTGA ATTCTCATGT TTACAAACTT GCTGTGTAAA |
| 2251 | CCTTGTTCCT TAATTTAATA CCATTGGTTA AATAAAATTG GCTGCAACCA |
| 2301 | ATTACTGGAG GGATTAGAGG TAGGGGCTT TTGAGTTACC TGTTTGGAGA |
| 2351 | TGGAGAAGGA GAGAGGAGAG ACCAAGAGGA GAAGGAGGAA GGAGAGGAGA |
| 2401 | GGAGAGGAGA GGAGAGGAGA GGAGAGGAGA GGAGAGGAGA GGAGAGGAGA |
| 2451 | GGCTGCCGTG AGGGGAGAGG GACCATGAGC CTGTGGCCAG GAGAAACAGC |
| 2501 | AAGTATCTGG GGTACACTGG TGAGGAGGTG GCCAGGCCAG CAGTTAGAAG |
| 2551 | AGTAGATTAG GGGTGACCTC CAGTATTTGT CAAAGCCAAT TAAAATAACA |
| 2601 | AAAAAAAAAA AAAAGCGGCC GCTCTAGA |

Fig. 1B

```
  1 MPRGPVAALL LLILHGAWSC LDLTCYTDYL WTITCVLETR SPNPSILSLT
 51 WQDEYEELQD QETFCSLHRS GHNTTHIWYT CHMRLSQFLS DEVFIVNVTD
101 QSGNNSQECG SFVLAESIKP APPLNVTVAF SGRYDISWDS AYDEPSNYVL
151 RGKLQYELQY RNLRDPYAVR PVTKLISVDS RNVSLLPEEF HKDSSYQLQV
201 RAAPQPGTSF RGTWSEWSDP VIFQTQAGEP EAGWDPHMLL LLAVLIIVLV
251 FMGLKIHLPW RLWKKIWAPV PTPESFFQPL YREHSGNFKK WVNTPFTASS
301 IELVPQSSTT TSALHLSLYP AKEKKFPGLP GLEEQLECDG MSEPGHWCII
351 PLAAGQAVSA YSEERDRPYG LVSIDTVTVG DAEGLCVWPC SCEDDGYPAM
401 NLDAGRESGP NSEDLLLVTD PAFLSCGCVS GSGLRLGGSP GSLLDRLRLS
451 FAKEGDWTAD PTWRTGSPGG GSESEAGSPP GLDMDTFDSG FAGSDCGSPV
501 ETDEGPPRSY LRQWVVRTPP PVDSGAQSS
```

Fig. 2

```
huMU-1    ................GTCGACTGGAGGCCCAGCTGCCCGTCATCA   30
          ┌151      ||  |      ||||||  |||||| |
murMU-1   CAGCCCTACTGTCTTCCTCTGTGTAGGCTCTGCCCAGATGCCCGGC....  196 huMU-1    GAGTGACAGGTCTTATGACAGCCTGATTGGTGACTCGGGCTGGGTGTGGA   80
          ||  |  ||| |   |||    ||  |||||||||  ||| | ||||
murMU-1   TGGTCCTCAGCCTCAGGACTATCTCAGCAGTGACTC.CCCTGATTCTGGA  245 huMU-1    TTCTCACCCCAGGCCTCTGCCTGCTTTCTCAGACCCTCATCT...GTCAC  127
          | ||||  |  |  ||||||   ||||| | ||||| ||    |||
murMU-1   CTTGCACCTGACTGAACTCCTGCCCACCTCAAACCTTCACCTCCCACCAC  295 huMU-1    CCCCACGCTGAACCCAGCTG......CCACCCCAGAAGCCCATCAGACT  171
          | ||| ||  |||   ||||      ||||||||||| |||||| |  |
murMU-1   CACCACTCCGAGTCCCGCTGTGACTCCCACGCCCAGGAGACCACCCAAGT  345 huMU-1    GCCCCAGCACACGGAATGGATTTCTGAGAAAGAAGCCGAAACAGAAGGC   221
          |  ||||||  |||||||| ||||||||||| ||  ||| ||| ||||
murMU-1   G.CCCCAGCCTAAAGAATGGCTTTCTGAGAAAGACCCTGAAGGAGTAGGT  394 huMU-1    CCGTGGGAGTCAGCATGCCGCGTGGCTGGGCCGCCCCCTTGCTCCTGCTG  271
          |  || |  ||||||||||   |||   |  |  || ||||| ||||||
murMU-1   C..TGGGACACAGCATGCCCCGGGGCCCAGTGGCTGCCTTACTCCTGCTG  442 huMU-1    CTGCTCCAGGGAGGCTGGGGCTGCCCCGACCTCGTCTGCTACACCGATTA  321
          | ||||| ||||| || || ||||| |||||| ||||||||| | ||||
murMU-1   ATTCTCCATGGAGCTTGGAGCTGCCTGGACCTCACTTGCTACACTGACTA  492 huMU-1    CCTCCAGACGGTCATCTGCATCCTGGAAATGTGGAACCTCCACCCCAGCA  371
          |||| |||| ||||| || | ||||| || || ||||  ||||||||||
murMU-1   CCTCTGGACCATCACCTGTGTCCTGGAGACACGGAGCCCCAACCCCAGCA  542 huMU-1    CGCTCACCCTTACCTGGCAAGACCAGTATGAAGAGCTGAAGGACGAGGCC  421
          | ||||| ||||||||||||||  |||||||| | |||| | ||||| |
murMU-1   TACTCAGTCTCACCTGGCAAGATGAATATGAGGAACTTCAGGACCAAGAG  592 huMU-1    ACCTCCTGCAGCCTCCACAGGTCGGCCCACAATGCCACGCATGCCACCTA  471
          |||| |||||||||  ||||||| ||||||||  ||||| | ||    |
murMU-1   ACCTTCTGCAGCCTACACAGGTCTGGCCACAACACCACATATATGGTA   642 huMU-1    CACCTGCCACATGGATGTATTCCACTTCATGGCCGACGACATTTTCAGTG  521
          ||| ||||| |||||  | ||| | | |||| || | || |||||| ||
murMU-1   CACGTGCCATATGCGCTTGTCTCAATTCCTGTCCGATGAAGTTTTCATTG  692 huMU-1    TCAACATCACAGACCAGTCTGGCAACTACTCCCAGGAGTGTGGCAGCTTT  571
          ||||  | || |||||||||||||| |||||||||||||||||||||||
murMU-1   TCAATGTGACGGACCAGTCTGGCAACAACTCCCAAGAGTGTGGCAGCTTT  742 huMU-1    CTCCTGGCTGAGAGCATCAAGCCGGCTCCCCCTTTCAACGTGACTGTGAC  621
          | ||||||||||||||||||  ||||||||||| ||||||||||||| |
murMU-1   GTCCTGGCTGAGAGCATCAAACCAGCTCCCCCCTTGAACGTGACTGTGGC  792 huMU-1    CTTCTCAGGACAGTATAATATCTCCTGGCGCTCAGATTACGAAGACCCTG  671
          |||||||||||  |||| |||||||||| ||||| |||  |||| |||
murMU-1   CTTCTCAGGACGCTATGATATCTCCTGGGACTCAGCTTATGACGAACCCT  842 huMU-1    CCTTCTACATGCTGAAGGGCAAGCTTCAGTATGAGCTGCAGTACAGGAAC  721
          || |||| | ||||| ||||||||| ||| | ||||||||||| ||||
murMU-1   CCAACTACGTGCTGAGGGGCAAGCTACAATATGAGCTGCAGTATCGGAAC  892
```

Fig. 3A

```
huMU-1   CGGGGAGACCCCTGGGCTGTGAGTCCGAGGAGAAAGCTGATCTCAGTGGA   771
         | ||||||| |||||||||||||| ||  |||||||||||||||||||||
murMU-1  CTCAGAGACCCCTATGCTGTGAGGCCGGTGACCAAGCTGATCTCAGTGGA   942 huMU-1   CTCAAGAAGTGTCTCCCTCCTCCCCCTGGAGTTCCGCAAAGACTCGAGCT   821
         ||||||||  ||||| ||  ||||| ||||||||| |||||| | ||||
murMU-1  CTCAAGAAACGTCTCTCTTCTCCCTGAAGAGTTCCACAAAGATTCTAGCT   992 huMU-1   ATGAGCTGCAGGTGCGGGCAGGGCCCATGCCTGGCTCCTCCTACCAGGGG   871
         |  ||||||||||||||||||  ||| |||| |||| |||| |||||||
murMU-1  ACCAGCTGCAGGTGCGGGCAGCGCCTCAGCCAGGCACTTCATTCAGGGGG   1042 huMU-1   ACCTGGAGTGAATGGAGTGACCCGGTCATCTTTCAGACCCAGTCAGAGGA   921
         ||||||||||| ||||||||||| ||||||||||||||||||  | |||
murMU-1  ACCTGGAGTGAGTGGAGTGACCCCGTCATCTTTCAGACCCAGGCTGGGGA   1092 huMU-1   GTTAAAGGAAGGCTGGAACCCTCACCTGCTGCTTCTCCTCCTGCTTGTCA   971
         |   ||| ||||||||| ||||||| |||||   ||||| ||||  |||
murMU-1  GCCCGAGGCAGGCTGGGACCCTCACATGCTG...CTGCTCCTGGCTGTCT   1139 huMU-1   TAGTCTTCATTCCTGCCTTCTGGAGCCTGAAGACCCATCCATTGTGGAGG   1021
          | ||| ||| || |||||| || ||||||||| |||| ||| ||||||
murMU-1  TGATCATTGTCCTGGTTTTCATGGGTCTGAAGATCCACCTGCCTTGGAGG   1189 huMU-1   CTATGGAAGAAGATATGGG...CCGTCCCCAGCCCTGAGCGGTTCTTCAT   1068
         |||||||  |||||||||    | |   ||||||||||| ||||||||
murMU-1  CTATGGAAAAAGATATGGGCACCAGTGCCCACCCCTGAGAGTTTCTTCCA   1239 huMU-1   GCCCCTGTACAAGGGCTGCAGCGGAGACTTCAAGAAATGGGTGGGTGCAC   1118
         ||||||||||| | |||||| |||  | ||||||||||||||  |  |
murMU-1  GCCCCTGTACAGGGAGCACAGCGGGAACTTCAAGAAATGGGTTAATACCC   1289 huMU-1   CCTTCACTGGCTCCAGCCTGGAGCTGGGACCCTGGAGCCCAGAGGTGCCC   1168
         | |||||  ||||||||| ||||| ||| |||   | ||| || | |||
murMU-1  CTTTCACGGCCTCCAGCATAGAGTTGGTGCCACAGAGTTCCACAACAACA   1339 huMU-1   TCCACCCTGGAGGTGTACAGCTGCCACCCACCACGGAGCCCGGCCAAGAG   1218
         |  ||| | |   ||             ||   | |     |||||| |
murMU-1  TCAGCCTTACATCTGT...............CATTGTATCCAGCCAAGGA   1374 huMU-1   GCTGCAGCTCACGGAGCTACAAGAACCAGCAGAGCTGGTGGAGTCTGACG   1268
         | |||  || |||||||| ||||| | ||||  |||| ||||||||| |
murMU-1  GAAGAAGTTCCCGGGGCTGCCGGGTCTGGAAGAGCAACTGGAGTGTGATG   1424 huMU-1   GTGTGCCCAAGCCCAGCTTCTGG.........CCGACAGCCCAGAACTCG   1309
         | ||| |    || || || ||          ||||||  |  ||||
murMU-1  GAATGTCTGAGCCTGGTCACTGGTGCATAATCCCCTTGGCAGCTGGCCAA   1474 huMU-1   GGGGGCTCAGCTTACAGTGAGGAGAGGGATCGGCCATACGGCCTGGTGTC   1359
         | | ||||||| |||||||||||||| |||||||||| |||||||||||
murMU-1  GCGGTCTCAGCCTACAGTGAGGAGAGAGACCGGCCATATGGTCTGGTGTC   1524 huMU-1   CATTGACACAGTGACTGTGCTAGATGCAGAGGGGCCATGCACCTGGCCCT   1409
         |||||||||||||||||||| ||||||||||||||  | | ||||||||
murMU-1  CATTGACACAGTGACTGTGGGAGATGCAGAGGGCCTGTGTGTCTGGCCCT   1574 huMU-1   GCAGCTGTGAGGATGACGGCTACCCAGCCCTGGACCTGGATGCTGGCCTG   1459
         | |||||||||||||| |||| |||||||||| ||||||||||||||| |
murMU-1  GTAGCTGTGAGGATGATGGCTATCCAGCCATGAACCTGGATGCTGGCCGA   1624 huMU-1   GAGCCCAGCCCAGGCCTAGAGGACCCACTCTTGGATGCAGGGACCACAGT   1509
         ||| | ||||| |||||  ||||||| ||| ||||| | |||||| |
murMU-1  GAGTCTGGCCCTAATTCAGAGGATCTGCTCTTGGTCACAGACCCTGCTTT   1674
```

Fig. 3B

```
huMU-1   CCTGTCCTGTGGCTGTGTCTCAGCTGGCAGCCCTGGGCTAGGAGGGCCCC  1559
         |||||  || ||||||||||||  |   |   ||||  |||||  |||
murMU-1  TCTGTCTTGCGGCTGTGTCTCAGGTAGTGGTCTCAGGCTTGGAGGCTCCC  1724 huMU-1   TGGGAAGCCTCCTGGACAGACTAAAGCCACCCCTTGCAGATGGGGAGGAC  1609
         | || ||||| ||||||||| | | ||| ||  |||||| |  |||| |
murMU-1  CAGGCAGCCTACTGGACAGGTTGAGGCTGTCATTTGCAAAGGAAGGGGAC  1774 huMU-1   TGGGCTGGGGGACTGCCCTGGGGTGGCCGGTCACCTGGAGGGGTCTCAGA  1651
         ||| |  |    |||    |||   ||| |   |||| |||| ||||  
murMU-1  TGGACAGCAGACCCAACCTGGAGAACTGGGTCCCCAGGAGGGGCTCTGA   1824 huMU-1   GAGTGAGGCGGGCTCACCCCTGGCCGGCCTGGATATGGACACGTTTGACA  1709
         ||||| ||| ||  ||||||   |||  ||||||| |||||| |||||| 
murMU-1  GAGTGAAGCAGGTTCCCCCC...CTGGTCTGGACATGGACACATTTGACA  1871 huMU-1   GTGGCTTTGTGGGCTCTGACTGCAGCAGCCCTGTGGAGTGTGACTTCACC  1759
         |||||||| | || || |||||  ||||||||||||| | |        
murMU-1  GTGGCTTTGCAGGTTCAGACTGTGGCAGCCCCGTGGAGACT.........  1912 huMU-1   AGCCCCGGGGACGAAGGACCCCCCCGGAGCTACCTCCGCCAGTGGGTGGT  1809
                  || |||||||||||||  |||||| |||||||||||||||
murMU-1  ........GATGAAGGACCCCCTCGAAGCTATCTCCGCCAGTGGGTGGT   1953 huMU-1   CATTCCTCCGCCACTTTCGAGCCCTGGACCCCAGGCCAGCTAATGAGGCT  1859
         |  | ||| || |    |  |||| ||   ||||  |||||        
murMU-1  CAGGACCCCTCCACCTGTGGACAGTGGAGCCCAGAGCAGCTA........  1995 huMU-1   GACTGGATGTCCAGAGCTGGCCAGGCCACTGGGCCCTGAGCCAGAGACAA  1909
            |||   |    |||  ||||  | || | | ||  |||        
murMU-1  .GCATATAATAACCAGCTATAGTGAGAAGAGGCCTCTGAGCC........  2036
                                                        ┌1960
huMU-1   TGGGCCTTTGAGCCTGATGTTTACAGTGTCTGTGTGTGTGTGCATATG    2009
         |||  |  ||  |||   |  | ||||||||||||||||||||  |||
murMU-1  TGGCATTTACAGTGTGAACATGTAGGGGTGTGTGTGTGTGTGTGTGTG    2086
                                         . 2050─┐ ┌─2151 .
huMU-1   TGTGTGTGCATATGCATGTGTGTGTGTGTGTGTGTCTTACTGGACTCA    2159
         ||||||||  |  | || |||||||||||||||||||||||    | |
murMU-1  TGTGTGTGTGTGTGTGTGTGTGTGTGTGTGTGTGTCTT.GGGTTGTGT    2135 huMU-1   CGGAGCTCACCCATGTGCACAAGTGTGCACAGTAAACGTGTTTGTGGTCA  2209
         |||  || |||||    ||  |                  ||||  |  |
murMU-1  GTTAGCACATCCATGTTGGGATTTG..............GTCTGTTGCTA  2171 huMU-1   ACAGATGACAACAGCCGTCCTCCCTCCTAGGGTCTTGTGTTGCAAGTTGG  2259
         | ||    |   |||  |||||  || |||||    || ||||   |||
murMU-1  TGTATTGTAATGCTAAATTCTCTACCCAAAGTTCTAGGCCTACGAGTGAA  2221 huMU-1   TCCACAGCATCTCCGGGGCTTTGTGGGATCAGGGCATTGCCTGTGACTGA  2309
         | ||   ||| |     |||| ||| | || |  || ||  |||| |  |
murMU-1  TTCTCATGTTTACAAACTTGCTGTGTAAACCTTG...TTCCTTAATTTAA  2268 huMU-1   GGCGGAGCCCAGCCCTCCAGCGTCTGCCTCCAGGAGCTGCAAGAAGTCCA  2359
            |||| |||| ||| |  || |||  ||  ||   |||||   |  | 
murMU-1  TACCATTGGTTAAATAAAATTGGCTGCAACCAATTACTGGAGGGATTAGA  2318 huMU-1   TATTG.....TTCCTTATCACCTGCCAACAGGAAGCGAAAGGGGATGGAG  2404
         | |||     |  |||||  |  |  |||| | |  || || ||||  |
murMU-1  GGTAGGGGCTTTTGAGTTACCTGTTTGGAGATGGAGAAGGAGAGAGGAG   2368
```

Fig. 3C

```
huMU-1   TGAGCCCATGGTGACCTCGGGAATGGCAATTTTTTGGGCGGCCCCTGGAC   2454
         ||| || ||  |||  ||| |          ||| |           |
murMU-1  AGACCAAGAGGAGAAGGAGGAAGGAGAGGAGAGGAGAGGAGAGGAGAGGA   2418 huMU-1   GAAGGTCTGAATCCCGACTCTGATACCTTCTGGCTGTGCTACCTGAGCCA   2504
         |||  ||   ||||  ||   ||  ||          |||    || |
murMU-1  GAGGAGAGGAGAGGAGA.GGAGAGGAGAGGAGAGGCTGCCGTGAGGGGAG   2467 huMU-1   AGTCGCCTCCCCTCTCTGGGCTAGAGTTTCCTTATCCAGACAGTGGGGAA   2554
         | |  ||       || ||||  |||  |     |||         |||
murMU-1  AGGGACCATGAGCCTGTGGCCAGGAGAAACAGCA...........AGTA   2505 huMU-1   GGCATGACACACCTGGGGGAAATTGGCGATGTCACCCGTGTACGGTACGC   2604
         |  ||||  |  |||||   ||| |||| ||||   ||  ||   |
murMU-1  TCTGGGGTACACTGGTGAGGAGGTGGCCAGGCCAGC..AGTTAGAAGAGT   2553 huMU-1   AGCCCAGAGCAGACCCTCAATAAACGTCAGCTTCCTTCAAAAAAAAAAAA   2654
         ||  |||  ||||  || || |||   |||   |  ||||||||  ||||
murMU-1  AGATTAGGGGTGACCTCCAGTATTTGTCAAAGCCAATTAAAATAACAAAA   2603 huMU-1   AAAAATCTAGA..............   2665
         |||||   ||
murMU-1  AAAAAAAAAAAGCGGCCGCTCTAGA   2628
```

Fig. 3D

```
Human MU-1    MPRGWAAPLLLLLLQGGWGCPDLVCYTDYLQTVICILEMWNLHPSTLTLT  50
              ||||  |  ||||:|  |  |  |  ||  ||||||| |: |:||  . .|| |.||
MurineMU-1    MPRGPVAALLLLILHGAWSCLDLTCYTDYLWTITCVLETRSPNPSILSLT  50

Human MU-1    WQDQYEELKDEATSCSLHRSAHNATHATYTCHMDVFHFMADDIFSVNITD  100
              |||:||||.|:  |  |||||||  || ||  |||||  .   |:.|::|  ||:||
MurineMU-1    WQDEYEELQDQETFCSLHRSGHNTTHIWYTCHMRLSQFLSDEVFIVNVTD  100

Human MU-1    QSGNYSQECGSFLLAESIKPAPPFNVTVTFSGQYNISWRSDYEDPAFYML  150
              ||||  ||||||||.||||||||||||  ||||  |||.|.|||  |  |::|.  |.|
MurineMU-1    QSGNNSQECGSFVLAESIKPAPPLNVTVAFSGRYDISWDSAYDEPSNYVL  150

Human MU-1    KGKLQYELQYRNRGDPWAVSPRRKLISVDSRSVSLLPLEFRKDSSYELQV  200
              :|||||||||||  ||:||  |  ||||||||.|||||  ||  |||||:|||
MurineMU-1    RGKLQYELQYRNLRDPYAVRPVTKLISVDSRNVSLLPEEFHKDSSYQLQV  200

Human MU-1    RAGPMPGSSYQGTWSEWSDPVIFQTQSEELKEGWNPHLLLLLLLVIVFIP  250
              ||  |  ||.|:.|||||||||||||||||.  |  .  ||.||:||||  ..|: :
MurineMU-1    RAAPQPGTSFRGTWSEWSDPVIFQTQAGEPEAGWDPHMLLLLAVLIIVL.  249

Human MU-1    AFWSLKTHPLWRLWKKIWA.VPSPERFFMPLYKGCSGDFKKWVGAPFTGS  299
              |  ||  |  |||||||||  ||-||  ||  |||:  ||-|||||  |||  |
MurineMU-1    VFMGLKIHLPWRLWKKIWAPVPTPESFFQPLYREHSGNFKKWVNTPFTAS  299

Human MU-1    SLELGPWSPEVPSTLEVYSCHPPRSPAKRLQLTELQEPAELVESDGVPKP  349
              |:||||  |  ||  |  |||  .  |  |.|  ||..|
MurineMU-1    SIELVPQSSTTTSAL.....HLSLYPAKEKKFPGLPGLEEQLECDGMSEP  344

Human MU-1    SFW...PTAQNSGGSAYSEERDRPYGLVSIDTVTVLDAEGPCTWPCSCED  396
              |  ||  |||||||||||||||||||||||||| ||||  |  |||||||
MurineMU-1    GHWCIIPLAAGQAVSAYSEERDRPYGLVSIDTVTVGDAEGLCVWPCSCED  394

Human MU-1    DGYPALDLDAGLEPSPGLEDPLLDAGTTVLSCGCVSAGSPGLGGPLGSLL  446
              ||||:.||||  |  |  || ||  |||||||  |||  |||||
MurineMU-1    DGYPAMNLDAGRESGPNSEDLLLVTDPAFLSCGCVSGSGLRLGGSPGSLL  444

Human MU-1    DRLKPPLADGEDWAGGLPWGGRSPGGVSESEAGSPLAGLDMDTFDSGFVG  496
              |||:  |  ||  |  ||||  |||||||  ||||||||||  |
MurineMU-1    DRLRLSFAKEGDWTADPTWRTGSPGGGSESEAGSP.PGLDMDTFDSGFAG  493

Human MU-1    SDCSSPVECDFTSPGDEGPPRSYLRQWVV.IPPPLSSPGPQAS*  539
              |||  ||||  ||||||||||||||  |||.  |  |  |.|
MurineMU-1    SDCGSPVET......DEGPPRSYLRQWVVRTPPPVDS.GAQSS.  529
```

Fig. 4

```
                    1                                                          50
        humu    ~~~MPRGWAA PLLLLL..LQ GGWG......            CPDLVCYTDY LQTVICILEM
        mousemu ~~~MPRGPVA ALLLLI..LH GAWS......            CLDLTCYTDY LWTITCVLET
        humil2rbc MAAPALSWRL PLLILLLPLA TSWASAAVNG          TSQFTCFYNS RANISCVWSQ
                   51                                                         100
        humu     WN..LHPSTL TLTWQDQYEE LKDEATSCSL HRSAHNATHA TYTCHM....
        mousemu  RS..PNPSIL SLTWQDEYEE LQDQETFCSL HRSGHNTTHI WYTCHM....
        humil2rbc DGALQDTSCQ VHAWPDR... .RRWNQTCEL ....LPVSQA SWACNLILGA
                   101                                                        150
        humu     .DVFHFMADD IFSVNITDQS GN..YSQECG SFLLAESIKP APPFNVTVTF
        mousem   .RLSQFLSDE VFIVNVTDQS GN..NSQECG SFVLAESIKP APPLNVTVAF
        humil2rbc PDSQKLTTVD IVTLRVLCRE GVRWRVMAIQ DFKPFENLRL MAPISLQVVH
                   151                                                        200
        humu     ..SGQYNISW RSDYEDPAFY MLKGKLQYEL QYRNRGDPWA VSPRRKLISV
        mousemu  ..SGRYDISW DSAYDEPSNY VLRGKLQYEL QYRNLRDPYA VRPVTKLISV
        humil2rbc VETHRCNISW E..ISQASHY FER.HLEFEA RTLSPGHTWE EAP...LLTL
                   201                                                        250
        humu     DSRSVSLLPL EFRKDSSYEL QVRAGPMPGS SYQGTWSEWS DPVIFQTQS.
        mousemu  DSRNVSLLPE EFHKDSSYQL QVRAAPQPGT SFRGTWSEWS DPVIFQTQA.
        humil2rbc KQKQEWICLE TLTPDTQYEF QVRVKPLQGE F..TTWSPWS QPLAFRTKPA
                   251                                                        300
        humu     ..EELKEGWN PHLLLLL... LLVIVFIPAF WSLKTHPLWR LWKKIWA.VP
        mousemu  ..GEPEAGWD PHMLLLL... AVLIIVL.VF MGLKIHLPWR LWKKIWAPVP
        humil2rbc ALGKDTIPWL GHLLVGLSGA FGFIILVYLL INCRNTGPW. LKKVLKCNTP
                   301                                                        350
        humu     SPERFFMPLY KGCSGDFKKW VGAPFTGSSL ELGPWSPEVP STLEVYSCHP
        mousemu  TPESFFQPLY REHSGNFKKW VNTPFTASSI ELVPQSSTTT SAL.....HL
        humil2rbc DPSKFFSQLS SEHGGDVQKW LSSPFPSSSF SPGGLAPEIS PLEVLERDKV
                   351                                                        400
        humu     PRSPAKRLQL TELQEPA..E LVESDGVPKP SFW...PTAQ NSGGSAYSEE
        mousemu  SLYPAKEKKF PGLPGLE..E QLECDGMSEP GHWCIIPLAA GQAVSAYSEE
        humil2rbc TQLLLQQDKV PEPASLSSNH SLTSCFTNQG YFFFHLPDAL EIEACQVYFT
                   401                                                        450
        humu     RDRPYGLVSI DTVTVLDAEG PC...TWPCS CEDDGYPALD LDAGLEPSPG
        mousemu  RDRPYGLVSI DTVTVGDAEG LC...VWPCS CEDDGYPAMN LDAGRESGPN
        humil2rbc YD.PYSEEDP DEGVAGAPTG SSPQPLQPLS GEDDAYCTF. ........PS
                   451                                                        500
        humu     LEDPLLDAGT TVLSCGCVSA GSPGLGGPLG SLLDRLKPPL AD..GEDWAG
        mousemu  SEDLLLVTDP AFLSCGCVSG SGLRLGGSPG SLLDRLRLSF AK..EGDWTA
        humil2rbc RDDLLLFS.P SLL..GGPSP PSTAPGGS.G AGEERMPPSL QERVPRDWDP
                   501                                                        550
        humu     GLPWGGRSPG GVSESEAGSP LAGLDMDTFD SGFVGSDCSS PVECDFTSPG
        mousemu  DPTWRTGSPG GGSESEAGSP .PGLDMDTFD SGFAGSDCGS PVET......
        humil2rbc Q.PLGPPTPG VPDLVDFQPP P...ELVLRE AGEEVPDAG. PRE.GVSFPW
                   551                              588
        humu     DEGPPRSYLR QWVVIPPPLS SPGPQAS*~~ ~~~~~~~~
        mousemu  DEGPPRSYLR QWVVRTPPPV DSGAQSS~~~ ~~~~~~~~
        humil2rbc SRPPGQGEFR ALNARLPLNT DAYLSLQELQ GQDPTHLV
```

MU-1, MEMBER OF THE CYTOKINE RECEPTOR FAMILY

CROSS-REFERENCE TO RELATED APPLICATIONS

The present application is a divisional application of U.S. patent application Ser. No. 11/957,891, filed Dec. 17, 2007, entitled "MU-1, MEMBER OF THE CYTOKINE RECEPTOR FAMILY," now U.S. Pat. No. 7,705,123, which is a continuation of U.S. patent application Ser. No. 09/569,384, filed May 11, 2000, now abandoned, which is a continuation-in-part of U.S. patent application Ser. No. 09/560,766, filed Apr. 28, 2000, now abandoned, which is a continuation of U.S. patent application Ser. No. 09/040,005, filed Mar. 17, 1998, now U.S. Pat. No. 6,057,128. The contents of the above-referenced patent applications are incorporated by reference herein in their entireties.

INCORPORATION OF SEQUENCE LISTING

The Sequence Listing filed on Jan. 28, 2010, created on Jan. 28, 2010, named 019970431004ST25.TXT, having a size in bytes of 39 kb, is hereby incorporated by reference herein in its entirety.

BACKGROUND OF THE INVENTION

Field of the Invention

The present invention relates to new members of the mammalian cytokine receptor family of proteins (including without limitation human and murine receptor proteins), fragments thereof and recombinant polynucleotides and cells useful for expressing such proteins.

A variety of regulatory molecules, known as hematopoietins, have been identified which are involved in the development and proliferation of the various populations of hematopoietic or blood cells. Most hematopoietins exhibit certain biological activities by interacting with a receptor on the surface of target cells. Cytokine receptors are commonly composed of one, two or three chains. Many cytokine receptors and some cytokines, such as IL-12 p40, are members of the hematopoietin receptor superfamily of proteins. Identification of new members of the hematopoietin receptor superfamily can be useful in regulation of hematopoiesis, in regulation of immune responses and in identification of other members of the hematopoietin superfamily, including cytokines and receptors.

It would be desirable to identify and determine the DNA and protein sequence for heretofore unknown members of the hematopoietin receptor superfamily.

SUMMARY OF THE INVENTION

In accordance with the present invention, polynucleotides encoding the MU-1 hematopoietin receptor superfamily chain are disclosed, including without limitation those from murine and human sources.

In certain embodiments, the invention provides an isolated polynucleotide comprising a nucleotide sequence selected from the group consisting of: (a) the nucleotide sequence of SEQ ID NO:1; (b) the nucleotide sequence of SEQ ID NO:1 from nucleotide 236 to nucleotide 1852; (c) the nucleotide sequence of SEQ ID NO:1 from nucleotide 299 to nucleotide 1852; (d) the nucleotide sequence of SEQ ID NO:1 from nucleotide 299 to nucleotide 943; (e) a nucleotide sequence varying from the sequence of the nucleotide sequence specified in any of (a)-(d) as a result of degeneracy of the genetic code; (f) a nucleotide sequence capable of hybridizing under stringent conditions to the nucleotide specified in any of (a)-(d); (g) a nucleotide sequence encoding a species homologue of the sequence of SEQ ID NO:2; and (h) an allelic variant of the nucleotide sequence specified in any of (a)-(d). Preferably, the nucleotide sequence encodes a protein having a biological activity of the MU-1 hematopoietin receptor superfamily chain. The nucleotide sequence may be operably linked to an expression control sequence.

The invention also provides isolated polynucleotides comprising a nucleotide sequence encoding a peptide or protein comprising an amino acid sequence selected from the group consisting of: (a) the amino acid sequence of SEQ ID NO:2; (b) the amino acid sequence of SEQ ID NO:2 from amino acids 22 to 538; (c) the amino acid sequence of SEQ ID NO:2 from amino acids 22 to 236; (d) the amino acid sequence of SEQ ID NO:2 from amino acids 1 to 236; and (e) fragments of (a)-(d) having a biological activity of the MU-1 hematopoietin receptor superfamily chain.

In another embodiment, the invention provides an isolated polynucleotide comprising a nucleotide sequence selected from the group consisting of: (a) the nucleotide sequence of SEQ ID NO:9; (b) a nucleotide sequence varying from the sequence of the nucleotide sequence specified in (a) as a result of degeneracy of the genetic code; (c) a nucleotide sequence capable of hybridizing under stringent conditions to the nucleotide sequence specified in (a); and (d) an allelic variant of the nucleotide sequence specified in (a).

The invention also provides isolated polynucleotides comprising a nucleotide sequence encoding a peptide or protein comprising an amino acid sequence selected from the group consisting of: (a) the amino acid sequence of SEQ ID NO:10; and (b) fragments of (a) having a biological activity of the MU-1 hematopoietin receptor superfamily chain.

Host cells, preferably mammalian cells, transformed with the polynucleotides are also provided.

In other embodiments, the invention provides a process for producing a MU-1 protein. The process comprises: (a) growing a culture of the host cell of the present invention in a suitable culture medium; and (b) purifying the human MU-1 protein from the culture. Proteins produced according to these methods are also provided.

The present invention also provides for an isolated MU-1 protein comprising an amino acid sequence selected from the group consisting of: (a) the amino acid sequence of SEQ ID NO:2; (b) the amino acid sequence of SEQ ID NO:2 from amino acids 22 to 538; (c) the amino acid sequence of SEQ ID NO:2 from amino acids 22 to 236; (d) the amino acid sequence of SEQ ID NO:2 from amino acids 1 to 236; and (e) fragments of (a)-(d) having a biological activity of the MU-1 hematopoietin receptor superfamily chain.

The present invention also provides for an isolated MU-1 protein comprising an amino acid sequence selected from the group consisting of: (a) the amino acid sequence of SEQ ID NO:10; and (b) fragments of (a) having a biological activity of the MU-1 hematopoietin receptor superfamily chain.

Murine MU-1 (SEQ ID NO:10) has 65% identity with human MU-1.

In other preferred embodiments, the specified amino acid sequence is part of a fusion protein (with an additional amino acid sequence not derived from MU-1). Preferred fusion proteins comprise an antibody fragment, such as an Fc fragment.

Pharmaceutical compositions comprising a protein of the present invention and a pharmaceutically acceptable carrier are also provided.

The present invention further provides for compositions comprising an antibody that specifically reacts with a protein of the present invention.

In one embodiment, a MU-1 nucleic acid molecule of the invention is at least 65%, 70%, 75%, 80%, 85%, 86%, 87%, 88%, 89%, 90%, 91%, 92%, 93%, 94%, 95%, 96%, 97%, 98%, 99%, 99.5% or more identical to the nucleotide sequence (e.g., to the entire length of the nucleotide sequence) shown in SEQ ID NO:1 or 9.

In another preferred embodiment, the nucleic acid molecule consists of the nucleotide sequence shown in SEQ ID NO:1 or 9. In another preferred embodiment, the nucleic acid molecule includes a fragment of at least 50, 100, 200, 300, 400, 500, 600, 700, 800, 900, 1000, 1100, 1200, 1300, 1400, 1500, 1600, 1700, 1800, or more nucleotides (e.g., contiguous nucleotides) of the nucleotide sequence of SEQ ID NO:1 or 9, or a complement thereof.

In a preferred embodiment, the MU-1 protein family member has an amino acid sequence at least about 65%, 70%, 75%, 80%, 85%, 86%, 87%, 88%, 89%, 90%, 91%, 92%, 93%, 94%, 95%, 96%, 97%, 98%, 99%, 99.5% or more identical to the amino acid sequence of SEQ ID NO:2 or 10.

In another embodiment, the invention features fragments of the protein having the amino acid sequence of SEQ ID NO:2 or 10, wherein the fragment comprises at least 15, 20, 30, 40, 50, 60, 70, 80, 90, or 100 amino acids (e.g., contiguous amino acids) of the amino acid sequence of SEQ ID NO:2 or 10.

In another aspect, the present invention provides a method for detecting the presence of a MU-1 nucleic acid molecule, protein or polypeptide in a biological sample by contacting the biological sample with an agent capable of detecting a MU-1 nucleic acid molecule, protein or polypeptide such that the presence of a MU-1 nucleic acid molecule, protein or polypeptide is detected in the biological sample.

In another aspect, the present invention provides a method for detecting the presence of MU-1 activity in a biological sample by contacting the biological sample with an agent capable of detecting an indicator of MU-1 activity such that the presence of MU-1 activity is detected in the biological sample.

In another aspect, the invention provides a method for modulating MU-1 activity comprising contacting a cell capable of expressing MU-1 with an agent that modulates MU-1 activity such that MU-1 activity in the cell is modulated. In one embodiment, the agent inhibits MU-1 activity. In another embodiment, the agent stimulates MU-1 activity. In one embodiment, the agent is an antibody that specifically binds to a MU-1 protein. In another embodiment, the agent modulates expression of MU-1 by modulating transcription of a MU-1 gene or translation of a MU-1 mRNA. In yet another embodiment, the agent is a nucleic acid molecule having a nucleotide sequence that is antisense to the coding strand of a MU-1 mRNA or a MU-1 gene.

In one embodiment, the methods of the present invention are used to treat a subject having a disorder characterized by aberrant or unwanted MU-1 protein or nucleic acid expression or activity (e.g., an MU-1 associated disorder) by administering an agent that is a MU-1 modulator to the subject. In one embodiment, the MU-1 modulator is an MU-1 protein. In another embodiment, the MU-1 modulator is an MU-1 nucleic acid molecule. In yet another embodiment, the MU-1 modulator is a peptide, peptidomimetic, or other small molecule.

The present invention also provides diagnostic assays for identifying the presence or absence of a genetic alteration characterized by at least one of (i) aberrant modification or mutation of a gene encoding a MU-1 protein; (ii) misregulation of the MU-1 gene; and (iii) aberrant post-translational modification of an MU-1 protein, wherein a wild-type form of the gene encodes a protein with a MU-1 activity.

In another aspect the invention provides methods for identifying a compound that binds to or modulates the activity of a MU-1 protein, by providing an indicator composition comprising a MU-1 protein having MU-1 activity, contacting the indicator composition with a test compound, and determining the effect of the test compound on MU-1 activity (e.g., STAT phosphorylation, e.g., STAT 3 or STAT 5 phosphorylation) in the indicator composition to identify a compound that modulates the activity of a MU-1 protein.

BRIEF DESCRIPTION OF THE DRAWINGS

FIG. 1 depicts the full-length cDNA sequence of murine MU-1. The nucleotide sequence corresponds to nucleotides 1-2628 of SEQ ID NO:9. FIG. 1A depicts the cDNA sequence of murine MU-1 from nucleotide 1 to 1450, and FIG. 1B depicts the cDNA sequence of murine MU-1 from nucleotide 1451 to 2628.

FIG. 2 depicts the amino acid sequence of murine MU-1 (corresponding to the amino acids 1-529 of SEQ ID NO:10). There is a predicted leader sequence at amino acids 1-19, which was predicted by SPScan with a score of 10.1 (boldface type). There is a predicted transmembrane domain at amino acids 237-253 (underlined). Predicted signaling motifs include the following regions: Box 1: amino acids 265-274, and Box 2: amino acids 311-324 (bold and underlined); six tyrosines are located at amino acid positions 281, 319, 361, 369, 397, and 510. The WSXWS motif (SEQ ID NO:8) is located at amino acid residue 214 to amino acid residue 218 (in large, bold-face type). Potential STAT docking sites include amino acids 393-398 and amino acids 510-513.

FIG. 3 depicts the GAP comparison of human and murine MU-1 cDNA sequences (corresponding to nucleic acids 1-1909, 1960-2050, and 2151-2665 of SEQ ID NO:1 for the purposes of an alignment, and nucleic acids 151-2628 of SEQ ID NO:9, respectively). HuMU-1=human MU-1, murMU-1=murine MU-1. Gap Parameters: Gap Weight=50, Average Match=10.000, Length Weight=3, Average Mismatch=0.000. Percent Identity=66.116. FIG. 3A is a comparison of nucleotides 1-721 of human MU-1 of SEQ ID NO:1 to nucleotides 151-892 of mouse MU-1; FIG. 3B is a comparison of nucleotides 722-1509 of human MU-1 of SEQ ID NO:1 to nucleotides 893-1674 of mouse MU-1; FIG. 3C is a comparison of nucleotides 1510-2404 of human MU-1 of SEQ ID NO:1, wherein nucleic acids 1910-1959 and 2051-2150 of SEQ ID NO:1 have been removed for the purposes of the alignment, to nucleotides 1675-2368 of mouse MU-1; and FIG. 3D is a comparison of nucleotides 2405-2665 of human MU-1 of SEQ ID NO:1 to nucleotides 2369-2628 of mouse MU-1.

FIG. 4 depicts a GAP comparison of the human MU-1 protein (corresponding to amino acids 1-538 of SEQ ID NO:2) and the murine MU-1 protein (corresponding to amino acids 1-529 of SEQ ID NO:10): BLOSUM62 amino acid substitution matrix (Henikoff and Henikoff (1992) "Amino acid substitution matrices from protein blocks" *Proc. Natl. Acad. Sci. USA* 89:10915-19). Gap parameters=Gap Weight: 8, Average Match=2.912, Length Weight=2, Average Mismatch=-2.003. Percent Identity=65.267.

FIG. 5 depicts a multiple sequence alignment of the amino acids of human MU-1 (corresponding to SEQ ID NO:2), murine MU-1 (corresponding to SEQ ID NO:10), and human IL-2 beta chain (GenBank Accession No. AAA59143.1, corresponding to SEQ ID NO:17). Leader and transmembrane domains are underlined. Conserved cytokine receptor module motifs are indicated by bold-face type. Potential signaling regions are indicated by underlining and bold-face type.

DETAILED DESCRIPTION OF THE INVENTION

Figure 6:
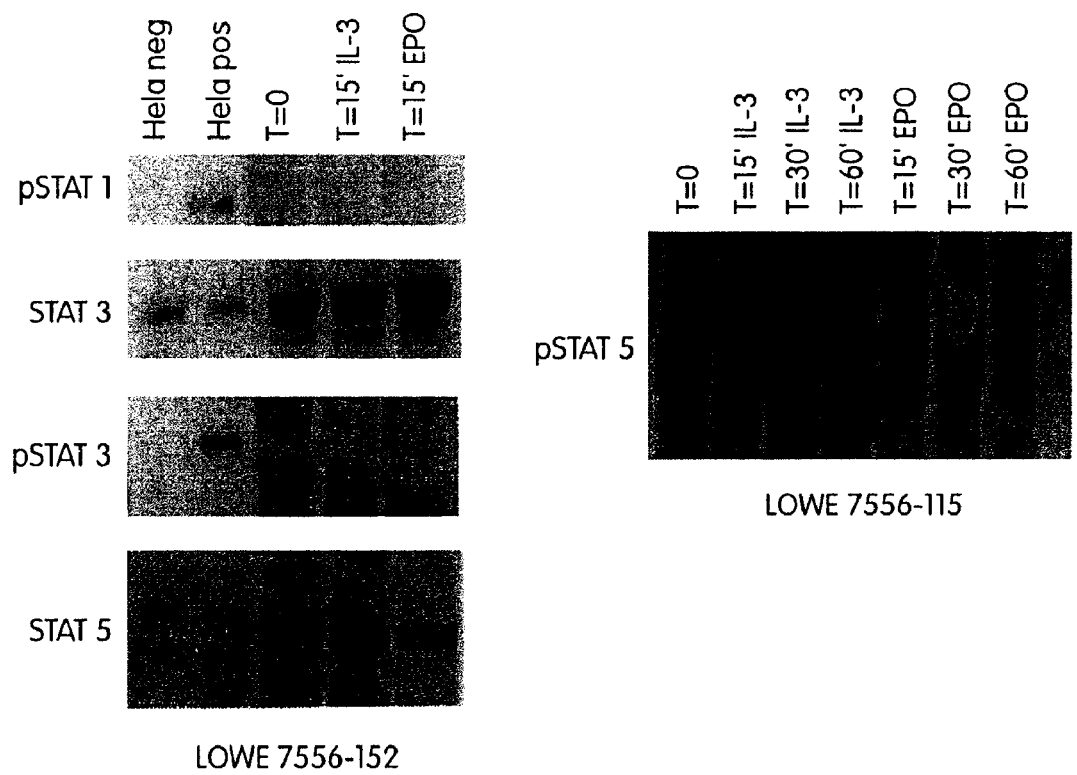
FIG. 6 depicts signaling through MU-1. MU-1 phosphorylates STAT 5 in Clone E7 EPO-MU-1 chimera. Under the conditions specified in Example 3, signaling through MU-1 results in the phosphorylation of STAT 5 at all time points tested. Treatment of controls or the chimeric BAF-3 cells with IL-3 resulted in phosphorylation of STAT 3, but not STAT 1 or STAT 5.

The inventors of the present application have for the first time identified and provided polynucleotides encoding the MU-1 hematopoietin receptor superfamily chain (hereinafter "MU-1" or "MU-1 protein"), including without limitation polynucleotides encoding human and murine MU-1.

In a particularly preferred embodiment, the MU-1 protein and nucleic acid molecules of the present invention are human MU-1 molecules. A 70-amino acid region of the human IL-5 receptor (LMTNAFISIIDDLSKYD-VQVRAAVSS MCREAGLWSEWSQPIYVGNDEHKPL-REWFVIVIMATICFILLIL, SEQ ID NO:3) was used to search the GenBank EST database using the TBLASTN algorithm. A sequence within the genomic BAC clone AC002303 from human chromosome 16p12 was identified with homology to this region, suggesting that this segment might encode a gene for a novel hematopoietin receptor. Examination of open reading frames within 1000 by of nucleotide 40,886 revealed a 270 by open frame which when used in a BLASTP search of GenPept exclusively identified members of the cytokine receptor family. A stop codon present at the end of this reading frame was interpreted as an indication of transition over an exon/intron border.

It was then determined whether RNA was transcribed from a gene contained within this BAC clone from chromosome 16p12. PCR primers were synthesized based on the largest ORF segment which contained peptide sequence conserved within the cytokine receptor family. Primers GAGTCCGAG-GAGAAAGCTGATCTCA (5p) (SEQ ID NO:4) and GAAA-GATGACCGGGTCACTCCATT (3p) (SEQ ID NO:5) were used in PCRs to screen phage libraries from various human tissues (Clontech). PCR products of the expected 164 by size that specifically hybridized to a $^{32}$P-labeled oligonucleotide of the sequence ACTCGAGCTATGAGCTGCAGGTGC GGGCA (SEQ ID NO:6) were observed in phage from lung, kidney, placenta and heart. Using the oligonucleotide ACTC-GAGCTATGAGCTGCAGGT GCGGGCA (SEQ ID NO:7) a full-length cDNA clone NN14-1b (MU-1) was identified, purified, and sequenced. The DNA sequence and the predicted amino acid sequence are shown in SEQ ID NO:1 and SEQ ID NO:2, respectively. The predicted amino acid sequence of the human MU-1 receptor chain includes a putative signal sequence from either amino acids 1-21 or 1-19. The mature human MU-1 is believed to have the sequence of amino acids 22-538 or 20-538 of SEQ ID NO:2. A transmembrane domain is found at amino acids 237-254.

In another particularly preferred embodiment, the MU-1 protein and nucleic acid molecules of the present invention are murine MU-1 molecules. To identify the polynucleotide sequence encoding the murine MU-1 protein, a partial fragment of the murine homolog of the MU-1 receptor was isolated by PCR from mouse cDNA using oligonucleotides derived from the human sequence, as described in Example 1. The DNA sequence of this fragment was determined, and two oligonucleotides were derived from an internal portion of this fragment with the following sequences:

```
TTGAACGTGACTGTGGCCTT (5p)    (SEQ ID NO: 13)

TGAATGAAGTGCCTGGCTGA (3p).   (SEQ ID NO: 14)
```

The oligonucleotides were used to amplify an internal 262 nucleotide fragment of the original PCR product (corresponding to nucleotides 781-1043 of the murine cDNA sequence of FIG. 1 and SEQ ID NO:9) to use as a hybridization probe to screen a cDNA library isolated from the 2D6 T cell line. DNA sequence was determined from two independent clones. Clone 6 was sequenced and confirmed to be the full-length murine homolog of human MU-1.

The full-length nucleotide sequence of murine MU-1 is shown in FIG. 1 (corresponding to nucleotides 1-2628 of SEQ ID NO:9). The nucleotide sequence has a predicted leader sequence at nucleotides 407-463, coding sequence at nucleotides 407-1993, and a termination codon at nucleotides 1994-1996. Nucleotides 1-406 correspond to the 5' untranslated region and nucleotides 1997-2628 correspond to the 3' untranslated region. The predicted protein sequence of murine MU-1 is shown in FIG. 2 (corresponding to amino acids 1-529 of SEQ ID NO:10).

The murine MU-1 protein contains a predicted leader sequence determined by SPScan (score=10.1) (corresponding to amino acids 1-19 of SEQ ID NO:10), and a predicted transmembrane domain (corresponding to amino acids 237-253 of SEQ ID NO:10). Predicted signaling motifs include the following regions: Box 1: amino acids 265-274 of SEQ ID NO:10, Box 2: amino acids 311-324 of SEQ ID NO:10, six tyrosine residues at positions 281, 319, 361, 369, 397, and 510 of SEQ ID NO:10. Potential STAT docking sites include but are not limited to: STAT 5: EDDGYPA (corresponding to SEQ ID NO:18); STAT 3: YLQR (corresponding to SEQ ID NO:19).

The open reading frame of MU-1 encodes a novel member of the hematopoietin receptor family. In a preferred embodiment, MU-1 has a leader sequence, conserved cysteine pairs, PP, and WSXWS (SEQ ID NO:8) motifs characteristic of the family, as well as a transmembrane domain and an extensive cytoplasmic domain. MU-1 also contains a conserved PXPP as well as Box 1 and Box 2 signaling motifs in the cytoplasmic domain (see FIG. 5). These domains are conserved between murine MU-1 and human MU-1. Subsequent FASTA alignment of MU-1 sequence with GenPept showed greatest homology with human IL-2Rb (see FIG. 5).

The human MU-1 cDNA was deposited with the American Type Culture Collection on March 10, 1998, as accession number ATCC 98687.

By Northern analysis, as described in Example 4, murine MU-1 was detected in adult murine spleen, lung, and heart tissues. Human MU-1 was detected in adult human lymphoid tissues, PBLs, thymus, spleen and lymph node, and in fetal lung.

Any forms of MU-1 proteins of less than full length are encompassed within the present invention and are referred to herein collectively with full-length and mature forms as "MU-1" or "MU-1 proteins." MU-1 proteins of less than full length may be produced by expressing a corresponding fragment of the polynucleotide encoding the full-length MU-1 protein (SEQ ID NO:2 or SEQ ID NO:10). These corresponding polynucleotide fragments are also part of the present invention. Modified polynucleotides as described above may be made by standard molecular biology techniques, including construction of appropriate desired deletion mutants, sitedirected mutagenesis methods or by the polymerase chain reaction using appropriate oligonucleotide primers.

For the purposes of the present invention, a protein has "a biological activity of the MU-1 hematopoietin receptor superfamily chain" if it possesses one or more of the biological activities of the corresponding mature MU-1 protein. In one embodiment, MU-1 activity includes interaction with STAT molecules (e.g., STAT 5, STAT 3). In another embodiment, the MU-1 protein activity does not bind to any known cytokines.

MU-1 or active fragments thereof (MU-1 proteins) may be fused to carrier molecules such as immunoglobulins or immunoglobulin fragments. For example, soluble forms of the MU-1 may be fused through "linker" sequences to the Fc portion of an immunoglobulin. Other fusion proteins, such as those with GST, Lex-A or MBP, may also be used.

The invention also encompasses allelic variants of the nucleotide sequences as set forth in SEQ ID NO:1 and SEQ ID NO:9, that is, naturally occurring alternative forms of the isolated polynucleotide of SEQ ID NO:1 or SEQ ID NO:9 that also encode MU-1 proteins, preferably those proteins having a biological activity of MU-1. Also included in the invention are isolated polynucleotides that hybridize to the nucleotide sequence set forth in SEQ ID NO:1 or SEQ ID NO:9 under highly stringent conditions (for example, 0.1× SSC at 65° C.). Isolated polynucleotides which encode MU-1 proteins but which differ from the nucleotide sequence set forth in SEQ ID NO:1 or SEQ ID NO:9 by virtue of the degeneracy of the genetic code are also encompassed by the present invention. Variations in the nucleotide sequence as set forth in SEQ ID NO:1 or SEQ ID NO:9 that are caused by point mutations or by induced modifications are also included in the invention.

As used herein, the term "hybridizes under stringent conditions" is intended to describe conditions for hybridization and washing under which nucleotide sequences at least 60% identical to each other typically remain hybridized to each other. Preferably, the conditions are such that sequences at least about 70%, more preferably at least about 80%, even more preferably at least about 85% or 90% identical to each other typically remain hybridized to each other. Such stringent conditions are known to those skilled in the art and can be found in *Current Protocols in Molecular Biology*, John Wiley & Sons, NY (1989), 6.3.1-6.3.6. A preferred, nonlimiting example of stringent hybridization conditions is hybridization in 6× sodium chloride/sodium citrate (SSC) at about 45° C., followed by one or more washes in 0.2×SSC, 0.1% SDS at 50° C., preferably at 55° C., more preferably at 60° C., and even more preferably at 65° C. Ranges that span the above recited values, e.g., 55-60° C., or 50-65° C. are encompassed by the present invention. Preferably, an isolated nucleic acid molecule of the invention that hybridizes under stringent conditions to the sequence of SEQ ID NO:1 or 9 corresponds to a naturally occurring nucleic acid molecule. As used herein, a "naturally occurring" nucleic acid molecule refers to an RNA or DNA molecule having a nucleotide sequence that occurs in nature (e.g., encodes a natural protein).

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and nonidentical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-53) algorithm which has been incorporated into the GAP program in GCG software package, using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in GCG software package, using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of Myers and Miller ((1988) *Comput. Appl. Biosci.* 4:11-17), which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to MU-1 nucleic acid molecules of the invention. BLAST protein searches can be performed with the XBLAST program, score=100, wordlength=3 to obtain amino acid sequences homologous to MU-1 protein molecules of the invention. To obtain gapped alignments for comparison purposes, Gapped BLAST can be utilized as described in Altschul et al. (1997) *Nucleic Acids Res.* 25(17):3389-402. When utilizing BLAST and Gapped BLAST programs, the default parameters of the respective programs (e.g., XBLAST and NBLAST) can be used (see, The National Center for Biotechnology Information website).

The present invention also provides polynucleotides encoding homologues of the human MU-1 from other animal species, particularly other mammalian species. Species homologues can be identified and isolated by making probes or primers from the murine or human sequences disclosed herein and screening a library from an appropriate species, such as for example libraries constructed from PBMCs, thymus or testis of the relevant species.

The isolated polynucleotides of the invention may be operably linked to an expression control sequence such as the pMT2 or pED expression vectors disclosed in Kaufman et al. (1991) *Nuc. Acids Res.* 19:4485-90, in order to produce the MU-1 protein recombinantly. Many suitable expression control sequences are known in the art. General methods of expressing recombinant proteins are also known and are exemplified in Kaufman (1990) *Meth. Enzymol.* 185:537-66. As defined herein, "operably linked" means enzymatically or chemically ligated to form a covalent bond between the isolated polynucleotide of the invention and the expression control sequence, in such a way that the MU-1 protein is expressed by a host cell that has been transformed (transfected) with the ligated polynucleotide/expression control sequence.

A number of types of cells may act as suitable host cells for expression of the MU-1 protein. Any cell type capable of expressing functional MU-1 protein may be used. Suitable mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK, Rat2, BaF3, 32D, FDCP-1, PC12, M1x or C2C12 cells.

The MU-1 protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif. (the MaxBac® kit), and such methods are well known in the art, as described in Summers and Smith (1987) *Texas Agricultural Experiment Station Bulletin No.* 1555, incorporated herein by reference. Soluble forms of the MU-1 protein may also be produced in insect cells using appropriate isolated polynucleotides as described above.

Alternatively, the MU-1 protein may be produced in lower eukaryotes such as yeast or in prokaryotes such as bacteria. Suitable yeast strains include *Saccharomyces cerevisiae, Schizosaccharomyces pombe, Kluyveromyces* strains, *Candida*, or any yeast strain capable of expressing heterologous proteins. Suitable bacterial strains include *Escherichia coli, Bacillus subtilis, Salmonella typhimurium*, or any bacterial strain capable of expressing heterologous proteins.

Expression in bacteria may result in formation of inclusion bodies incorporating the recombinant protein. Thus, refolding of the recombinant protein may be required in order to produce active or more active material. Several methods for obtaining correctly folded heterologous proteins from bacterial inclusion bodies are known in the art. These methods generally involve solubilizing the protein from the inclusion bodies, then denaturing the protein completely using a chaotropic agent. When cysteine residues are present in the primary amino acid sequence of the protein, it is often necessary to accomplish the refolding in an environment that allows correct formation of disulfide bonds (a redox system). General methods of refolding are disclosed in Kohno (1990) *Meth. Enzym.* 185:187-95. EP 0433225 and U.S. Pat. No. 5,399,677 describe other appropriate methods.

The MU-1 protein of the invention may also be expressed as a product of transgenic animals, e.g., as a component of the milk of transgenic cows, goats, pigs, or sheep which are characterized by somatic or germ cells containing a polynucleotide sequence encoding the MU-1 protein.

The MU-1 protein of the invention may be prepared by growing a culture of transformed host cells under culture conditions necessary to express the desired protein. The resulting expressed protein may then be purified from the culture medium or cell extracts. Soluble forms of the MU-1 protein of the invention can be purified from conditioned media. Membrane-bound forms of MU-1 protein of the invention can be purified by preparing a total membrane fraction from the expressing cell and extracting the membranes with a nonionic detergent such as Triton X-100.

The MU-1 protein can be purified using methods known to those skilled in the art. For example, the MU-1 protein of the invention can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) or polyetheyleneimine (PEI) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of the MU-1 protein from culture supernatant may also include one or more column steps over such affinity resins as concanavalin A-agarose, heparin-toyopearl® or Cibacrom blue 3GA Sepharose®; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify the MU-1 protein. Affinity columns including antibodies to the MU-1 protein can also be used in purification in accordance with known methods. Some or all of the foregoing purification steps, in various combinations or with other known methods, can also be employed to provide a substantially purified isolated recombinant protein. Preferably, the isolated MU-1 protein is purified so that it is substantially free of other mammalian proteins.

MU-1 proteins of the invention may also be used to screen for agents that are capable of binding to MU-1. Binding assays using a desired binding protein, immobilized or not, are well known in the art and may be used for this purpose using the MU-1 protein of the invention. Purified cell based or protein based (cell free) screening assays may be used to identify such agents. For example, MU-1 protein may be immobilized in purified form on a carrier and binding or potential ligands to purified MU-1 protein may be measured.

MU-1 proteins, purified from cells or recombinantly produced, may be used as a pharmaceutical composition when combined with a pharmaceutically acceptable carrier. Such a composition may contain, in addition to MU-1 or inhibitor and carrier, various diluents, fillers, salts, buffers, stabilizers, solubilizers, and other materials well known in the art. The term "pharmaceutically acceptable" means a nontoxic material that does not interfere with the effectiveness of the biological activity of the active ingredient(s). The characteristics of the carrier will depend on the route of administration.

The pharmaceutical composition of the invention may also contain cytokines, lymphokines, or other hematopoietic factors such as M-CSF, GM-CSF, IL-1, IL-2, IL-3, IL-4, IL-5, IL-6, IL-7, IL-8, IL-9, IL-10, IL-11, IL-12, IL-14, IL-15, G-CSF, stem cell factor, and erythropoietin. The pharmaceutical composition may also include anti-cytokine antibodies. The pharmaceutical composition may contain thrombolytic or anti-thrombotic factors such as plasminogen activator and Factor VIII. The pharmaceutical composition may further contain other anti-inflammatory agents. Such additional factors and/or agents may be included in the pharmaceutical composition to produce a synergistic effect with isolated MU-1 protein, or to minimize side effects caused by the isolated MU-1 protein. Conversely, isolated MU-1 protein may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome. In the liposome, isolated MU-1 protein and pharmaceutically acceptable carriers are combined with amphipathic agents, such as lipids that exist in aggregated form, such as micelles, insoluble monolayers, liquid crystals, or lamellar layers, in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of isolated MU-1 protein is administered to a mammal. Isolated MU-1 protein may be administered in accordance with the method of the invention either alone or in combination with other therapies such as treatments employing cytokines, lymphokines or other hematopoietic factors. When coadministered with one or more cytokines, lymphokines or other hematopoietic factors, MU-1 protein may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering MU-1 protein in combination with cytokine(s), lymphokine(s), other hematopoietic factor(s), thrombolytic or anti-thrombotic factors.

Administration of MU-1 protein used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of MU-1 protein is administered orally, MU-1 protein will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% MU-1 protein, and preferably from about 25 to 90% MU-1 protein. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of MU-1 protein, and preferably from about 1 to 50% MU-1 protein.

When a therapeutically effective amount of MU-1 protein is administered by intravenous, cutaneous or subcutaneous injection, MU-1 protein will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to MU-1 protein an isotonic vehicle such as sodium chloride injection, Ringer's injection, dextrose injection, dextrose and sodium chloride injection, lactated Ringer's injection, or other vehicle as known in the art. The pharmaceutical composition of the present invention may also contain stabilizers, preservatives, buffers, antioxidants, or other additives known to those of skill in the art.

The amount of MU-1 protein in the pharmaceutical composition of the present invention will depend upon the nature and severity of the condition being treated, and on the nature of prior treatments that the patient has undergone. Ultimately, the attending physician will decide the amount of MU-1 protein with which to treat each individual patient. Initially, the attending physician will administer low doses of MU-1 protein and observe the patient's response. Larger doses of MU-1 protein may be administered until the optimal therapeutic effect is obtained for the patient, and at that point the dosage is not generally increased further. It is contemplated that the various pharmaceutical compositions used to practice the method of the present invention should contain about 0.1 µg to about 100 mg of MU-1 protein per kg body weight.

The duration of intravenous therapy using the pharmaceutical composition of the present invention will vary, depending on the severity of the disease being treated and the condition and potential idiosyncratic response of each individual patient. It is contemplated that the duration of each application of the MU-1 protein will be in the range of 12 to 24 hours of continuous intravenous administration. Ultimately the attending physician will decide on the appropriate duration of intravenous therapy using the pharmaceutical composition of the present invention.

The polynucleotide and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

Cytokine and Cell Proliferation/Differentiation Activity

A protein of the present invention may exhibit cytokine, cell proliferation (either inducing or inhibiting) or cell differentiation (either inducing or inhibiting) activity or may induce production of other cytokines in certain cell populations.

Many protein factors discovered to date, including all known cytokines, have exhibited activity in one or more factor-dependent cell proliferation assays, and hence the assays serve as a convenient confirmation of cytokine activity. The activity of a protein of the present invention is evidenced by any one of a number of routine factor-dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mole and CMK.

BAF-3 cells expressing huEPOR-huMU chimeric receptors proliferate in response to huEPO. In order to test the capacity for the MU receptor to signal through their cytoplasmic domain, BAF-3 cells were engineered to express EPOr/MU(cyto) chimeric receptors and assayed for $^3$H thymidine incorporation in the presence of EPO. BAF-3 cells expressing intact EPOr molecules proliferate in response to EPO while parent BAF-3 cells do not. The A5 clone, possessing the chimeric EPOr/MU(cyto) proliferates in response to EPO demonstrating that the cytoplasmic portion of MU-1 can sustain a proliferative signal. The BAF-3 cells which express EPOr on their surface also respond to EPO.

The activity of a protein of the invention may, among other means, be measured by the following methods:

Assays for T cell or thymocyte proliferation include without limitation those described in: *Current Protocols in Immunology*, J. E. Coligan et al. eds., Pub. Greene Publishing Associates and Wiley-Interscience (Chapter 3, In Vitro Assays for Mouse Lymphocyte Function 3.1-3.19; Chapter 7, Immunologic Studies in Humans); Takai et al. (1986) *J. Immunol.* 137:3494-500; Bertagnolli et al. (1990) *J. Immunol.* 145:1706-12; Bertagnolli et al. (1991) *Cell. Immunol.* 133:327-41; Bertagnolli et al. (1992) *J. Immunol.* 149:3778-83; Bowman et al. (1994) *J. Immunol.* 152:1756-61.

Assays for cytokine production and/or proliferation of spleen cells, lymph node cells or thymocytes include, without limitation, those described in: Kruisbeek and Shevach (1994) "Polyclonal T cell Stimulation" In *Current Protocols in Immunology*, J. E. Coligan et al. eds., Vol. 1, pp. 3.12.1-3.12.14, John Wiley and Sons, Toronto; and Schreiber (1994) "Measurement of Mouse and Human Interferon γ" In *Current Protocols in Immunology*. J. E. Coligan et al. eds., Vol. 1, pp. 6.8.1-6.8.8, John Wiley and Sons, Toronto.

Assays for proliferation and differentiation of hematopoietic and lymphopoietic cells include, without limitation, those described in: Bottomly et al. (1991) "Measurement of Human and Murine Interleukin 2 and Interleukin 4" In *Current Protocols in Immunology*, J. E. Coligan et al. eds., Vol. 1, pp. 6.3.1-6.3.12, John Wiley and Sons, Toronto; deVries et al. (1991) *J. Exp. Med.* 173:1205-11; Moreau et al. (1988) *Nature* 336:690-92; Greenberger et al. (1983) *Proc. Natl. Acad. Sci. USA* 80:2931-38, 1983; Nordan (1991) "Measurement of Mouse and Human Interleukin 6" In *Current Protocols in Immunology*, J. E. Coligan et al. eds., Vol. 1, pp. 6.6.1-6.6.5, John Wiley and Sons, Toronto; Smith et al. (1986) *Proc. Natl. Acad. Sci. USA* 83:1857-61; Bennett et al. (1991) "Measurement of Human Interleukin 11" In *Current Protocols in Immunology*. J. E. Coligan et al. eds., Vol. 1, p. 6.15.1, John Wiley and Sons, Toronto; Ciarletta et al. (1991) "Measurement of Mouse and Human Interleukin 9" In *Current Protocols in Immunology*, J. E. Coligan et al. eds., Vol. 1, p. 6.13.1, John Wiley and Sons, Toronto.

Assays for T cell clone responses to antigens (which will identify, among others, proteins that affect APC-T cell interactions as well as direct T cell effects by measuring proliferation and cytokine production) include, without limitation, those described in: *Current Protocols in Immunology*, J. E. Coligan et al. eds., Pub. Greene Publishing Associates and Wiley-Interscience (Chapter 3, In Vitro Assays for Mouse Lymphocyte Function, 3.1-3.19; Chapter 6, Cytokines and their Cellular Receptors; Chapter 7, Immunologic Studies in Humans); Weinberger et al. (1980) *Proc. Natl. Acad. Sci. USA* 77:6091-95; Weinberger et al. (1981) *Eur. J. Immunol.* 11:405-11; Takai et al. (1986) *J. Immunol.* 137:3494-500; Takai et al. (1988) *J. Immunol.* 140:508-12.

Immune Stimulating or Suppressing Activity

A protein of the present invention may also exhibit immune-stimulating or immune-suppressing activity, including without limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpesviruses, mycobacteria, *Leishmania* spp., *malaria* spp. and various fungal infections such as candidiasis. Of course, in this regard, a protein of the present invention may also be useful where a boost to the immune system generally may be desirable, e.g., in the treatment of cancer.

Autoimmune disorders which may be treated using a protein of the present invention include, for example, connective tissue disease, multiple sclerosis, systemic lupus erythematosus (SLE), rheumatoid arthritis, autoimmune pulmonary inflammation, Guillain-Barre syndrome, autoimmune thyroiditis, insulin-dependent diabetes mellitus, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

The MU-1 DNA also maps to the chromosomal locus for Crohn's disease. As a result, proteins of the present invention may be used to treat Crohn's disease and other inflammatory bowel diseases.

Using the proteins of the invention it may also be possible to regulate immune responses, in a number of ways. Downregulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process that requires continuous exposure of the T cells to the suppressive agent. Tolerance, which involves inducing nonresponsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Downregulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al. (1992) *Science* 257:789-92 and Turka et al. (1992) *Proc. Natl. Acad. Sci. USA* 89:11102-05. In addition, murine models of GVHD (see Paul ed. (1989) *Fundamental Immunology*, Raven Press, New York, pp. 846-47) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents that block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, SLE in MRL/lpr/lpr mice or NZB hybrid mice, murine autoimmune collagen arthritis, diabetes mellitus in NOD mice and BB rats, and murine experimental myasthenia gravis (see Paul ed. (1989) *Fundamental Immunology*, Raven Press, New York, pp. 840-856).

Upregulation of an antigen function (preferably a B lymphocyte antigen function), as a means of upregulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activating, T cells in vivo.

In another application, upregulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell-mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class I $\alpha$ chain protein and $\beta_2$ microglobulin protein or an MHC class II $\alpha$ chain protein and an MHC class II $\beta$ chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell-mediated immune response against the transfected tumor cell. Optionally, a gene encoding an antisense construct that blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell-mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: *Current Protocols in Immunology*, J. E. Coligan et al. eds., Pub. Greene Publishing Associates and Wiley-Interscience (Chapter 3, In Vitro Assays for Mouse Lymphocyte Function, 3.1-3.19; Chapter 7, Immunologic Studies in Humans); Herrmann et al. (1981) *Proc. Natl. Acad. Sci. USA* 78:2488-92; Herrmann et al. (1982) *J. Immunol.* 128:1968-74; Handa et al. (1985) *J. Immunol.* 135:1564-72; Takai et al. (1986) *J. Immunol.* 137:

3494-500; Takai et al. (1988) *J. Immunol.* 140:508-12; Bowman et al. (1987) *J. Virology* 61:1992-98; Bertagnolli et al. (1991) *Cell. Immunol.* 133:327-41; Brown et al. (1994) *J. Immunol.* 153:3079-92.

Assays for T cell-dependent immunoglobulin responses and isotype switching (which will identify, among others, proteins that modulate T cell-dependent antibody responses and that affect Th1/Th2 profiles) include, without limitation, those described in: Maliszewski (1990) *J. Immunol.* 144: 3028-33; and Mond and Brunswick (1991) "Assays for B cell Function: In vitro Antibody Production" In *Current Protocols in Immunology*, J. E. Coligan et al. eds., Vol. 1, pp. 3.8.1-3.8.16, John Wiley and Sons, Toronto.

Mixed lymphocyte reaction (MLR) assays (which will identify, among others, proteins that generate predominantly Th1 and CTL responses) include, without limitation, those described in: *Current Protocols in Immunology*, J. E. Coligan et al. eds., Pub. Greene Publishing Associates and Wiley-Interscience (Chapter 3, In Vitro Assays for Mouse Lymphocyte Function 3.1-3.19; Chapter 7, Immunologic Studies in Humans); Takai et al. (1986) *J. Immunol.* 137:3494-500; Takai et al. (1988) *J. Immunol.* 140:508-12; Bertagnolli et al. (1992) *J. Immunol.* 149:3778-83.

Dendritic cell-dependent assays (which will identify, among others, proteins expressed by dendritic cells that activate naive T cells) include, without limitation, those described in: Guery et al. (1995) *J. Immunol.* 134:536-44; Inaba et al. (1991) *J. Exp. Med.* 173:549-59; Macatonia et al. (1995) *J. Immunol.* 154:5071-79; Porgador et al. (1995) *J. Exp. Med.* 182:255-60; Nair et al. (1993) *J. Virol.* 67:4062-69; Huang et al. (1994) *Science* 264:961-65; Macatonia et al. (1989) *J. Exp. Med.* 169:1255-64; Bhardwaj et al. (1994) *J. Clin. Invest.* 94:797-807; Inaba et al. (1990) *J. Exp. Med.* 172:631-40.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al. (1992) *Cytometry* 13:795-808; Gorczyca et al. (1993) *Leukemia* 7:659-70; Gorczyca et al. (1993) *Cancer Res.* 53:1945-51; Itoh et al. (1991) *Cell* 66:233-43; Zacharchuk (1990) *J. Immunol.* 145:4037-45; Zamai et al. (1993) *Cytometry* 14:891-97; Gorczyca et al. (1992) *Internl. J. Oncol.* 1:639-48.

Assays for proteins that influence early steps of T cell commitment and development include, without limitation, those described in: Antica et al. (1994) *Blood* 84:111-17; Fine et al. (1994) *Cell. Immunol.* 155:111-22; Galy et al. (1995) *Blood* 85:2770-78; Toki et al. (1991) *Proc. Nat. Acad. Sci. USA* 88:7548-51.

Hematopoiesis Regulating Activity

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in vivo or ex vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. (1995) *Cell. Biol.* 15:141-51; Keller et al. (1993) *Mol. Cell. Biol.* 13:473-86; McClanahan et al. (1993) *Blood* 81:2903-15.

Assays for stem cell survival and differentiation (which will identify, among others, proteins that regulate lymphohematopoiesis) include, without limitation, those described in: Freshney (1994) "Methylcellulose Colony Forming Assays" In *Culture of Hematopoietic Cells*, Freshney et al. eds., pp. 265-68, Wiley-Liss Inc., New York; Hirayama et al. (1992) *Proc. Natl. Acad. Sci. USA* 89:5907-11; McNiece and Briddell (1994) "Primitive Hematopoietic Colony Forming Cells with High Proliferative Potential" In *Culture of Hematopoietic Cells*, Freshney et al. eds., pp. 23-39, Wiley-Liss Inc., New York; Neben et al. (1994) *Exp. Hematol.* 22:353-59; Ploemacher (1994) "Cobblestone Area Forming Cell Assay" In *Culture of Hematopoietic Cells*, Freshney et al. eds., pp. 1-21, Wiley-Liss Inc., New York; Spooncer et al. (1994) "Long Term Bone Marrow Cultures in the Presence of Stromal Cells" In *Culture of Hematopoietic Cells*, Freshney et al. eds., pp. 163-179, Wiley-Liss Inc., New York; Sutherland (1994) "Long Term Culture Initiating Cell Assay" In *Culture of Hematopoietic Cells*, Freshney et al. eds., pp. 139-162, Wiley-Liss Inc., New York.

Research Uses and Utilities

Polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al. (1993) *Cell* 75:791-803) to identify polynucleotides encoding the other protein with which binding occurs or to identify inhibitors of the binding interaction.

The proteins provided by the present invention can similarly be used in assays to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual" (1989) 2d ed., Cold Spring Harbor Laboratory Press, Sambrook, J., E. F. Fritsch and T. Maniatis, Eds., and "Methods in Enzymology: Guide to Molecular Cloning Techniques" (1987) Academic Press, Berger, S. L. and A. R. Kimmel, Eds.

Nutritional Uses

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

MU-1 proteins of the invention may also be used to immunize animals to obtain polyclonal and monoclonal antibodies which specifically react with the MU-1 protein and which may inhibit binding of ligands to the receptor. Such antibodies may be obtained using the entire MU-1 as an immunogen, or by using fragments of MU-1. Smaller fragments of the MU-1 may also be used to immunize animals. The peptide immunogens additionally may contain a cysteine residue at the carboxyl terminus, and are conjugated to a hapten such as keyhole limpet hemocyanin (KLH). Additional peptide immunogens may be generated by replacing tyrosine residues with sulfated tyrosine residues. Methods for synthesizing such peptides are known in the art, for example, as in Merrifield (1963) *J. Amer. Chem. Soc.* 85:2149-54; Krstenansky et al. (1987) *FEBS Lett.* 211:10.

Neutralizing or nonneutralizing antibodies (preferably monoclonal antibodies) binding to MU-1 protein may also be useful therapeutics for certain tumors and also in the treatment of conditions described above. These neutralizing monoclonal antibodies may be capable of blocking ligand binding to the MU-1 receptor chain.

All patent and literature references cited herein are incorporated by reference as if fully set forth. This invention is further illustrated by the following examples, which should not be construed as limiting.

Examples

Example 1

Isolation and Characterization of Murine MU-1 cDNAs

A partial fragment of the murine homolog of the MU-1 receptor was isolated by PCR using oligonucleotides derived from the human sequence. cDNA was prepared from RNA isolated from 17-day-old murine thymus and from the murine 2D6 T cell line. A DNA fragment of approximately 300 nucleotides was amplified from the cDNA by PCR with the following oligonucleotides, corresponding to regions 584-603 and 876-896, respectively, of the human cDNA sequence in FIG. 1 (corresponding to SEQ ID NO:1):

```
AGCATCAAGCCGGCTCCCCC  (5p)     (SEQ ID NO: 11)

CTCCATTCACTCCAGGTCCC  (3p)     (SEQ ID NO: 12)
```

Amplification was carried out using Taq polymerase in 1× Taq buffer containing 1.5 mM of magnesium chloride for 30 cycles at 94° C. for one minute, 50° C. for 1 minute, and 72° C. for 1 minute. The DNA sequence of this fragment was determined, and two oligonucleotides were derived from an internal portion of this fragment with the following sequences:

```
TTGAACGTGACTGTGGCCTT  (5p)     (SEQ ID NO: 13)

TGAATGAAGTGCCTGGCTGA  (3p)     (SEQ ID NO: 14)
```

The oligonucleotides were used to amplify an internal 262 nucleotide fragment of the original PCR product (corresponding to nucleotides 781-1043 of the murine cDNA sequence of FIG. 1, and SEQ ID NO:9) to use as a hybridization probe to screen a cDNA library isolated from the 2D6 T cell line. Filters were hybridized at 65° C. using standard 5×SSC hybridization conditions and washed into SSC at 65° C. Twenty clones were isolated that hybridized to the probe in a screen of 426,000 clones. DNA sequence was determined from two independent clones. Full length sequence of clone #6 confirmed that it was the full-length murine homolog of human MU-1 (SEQ ID NO:9).

The full-length nucleotide sequence of murine MU-1 is shown in FIG. 1 (corresponding to SEQ ID NO:9). The nucleotide sequence has a predicted leader sequence at nucleotides 407-463, coding sequence at nucleotides 407-1993, termination codon at nucleotides 1994-1996. Nucleotides 1-406 correspond to the 5' untranslated region and nucleotides 1997-2628 correspond to the 3' untranslated region.

The predicted protein sequence of murine MU-1 is shown in FIG. 2 (corresponding to SEQ ID NO:10). This murine MU-1 protein contains a predicted leader sequence determined by SPScan (score=10.1) (corresponding to amino acids 1-19 of SEQ ID NO:10), and a predicted transmembrane domain (corresponding to amino acids 237-253 of SEQ ID NO:10). Predicted signaling motifs include the following regions: Box 1: amino acids 265-274 of SEQ ID NO:10, Box 2: amino acids 311-324 of SEQ ID NO:10, six tyrosine residues at positions 281, 319, 361, 369, 397, and 510 of SEQ ID NO:10. Potential STAT docking sites include: STAT 5: EDDGYPA (SEQ ID NO:18), STAT 3:YLQR (SEQ ID NO:19).

Example 2

Comparison of Human and Murine MU-1

The GAP algorithm was used to compare the human and murine MU-1 amino acids. A comparison of the murine and human predicted protein sequences is shown in FIG. 4. The amino acids were 65.267% identical using the GAP algorithm. The alignment was generated by BLOSUM62 amino acid substitution matrix (Henikoff and Henikoff (supra)). Gap parameters=Gap Weight: 8, Average Match=2.912, Length Weight=2, Average Mismatch=-2.003. Percent Similarity=69.466.

A comparison of the human and murine cDNA nucleotide sequences is shown in FIG. 3. The DNA sequences are 66.116% identical when aligned using the GAP algorithm. Gap Parameters: Gap Weight=50, Average Match=10.000, Length Weight=3, Average Mismatch=0.000. Percent Similarity=66.198.

Both human and mouse MU-1 proteins are members of the Type 1 cytokine receptor superfamily. Evaluation of the sequence of both murine and human MU-1 reveals the presence of potential Box-1 and Box-2 signaling motifs. Six tyrosine residues are present in the cytoplasmic domain, and could also be important in signaling functions of MU-1. Comparison of the sequences of MU-1 with other members of the family suggested the presence of potential docking sites for STAT 5 and STAT 3.

Example 3

Determination of STAT Signaling Pathways Used by Human MU-1

BAF-3 cells were engineered to express a chimeric cytokine receptor consisting of the extracellular domain of the human EPO receptor and the intracellular domain of the MU-1 receptor. BAF-3 cells that expressed huEPOR/MU-1 (cyto) chimeric receptors proliferated in response to human soluble EPO. These cells were analyzed to determine which STAT molecules were phosphorylated in response to EPO signaling. Briefly, control unmodified parental BAF-3 cells and EPOR/MU chimeric BAF-3 cells were rested from IL-3-containing growth medium, and restimulated with either IL-3 or EPO for 0, 15, 30 and 60 minutes. The cells were pelleted and resuspended in ice cold lysis buffer containing orthovanadate, to preserve phosphorylated tyrosines. Equal amounts of cell lysate were electrophoresed by SDS-PAGE and blotted onto nitrocellulose membranes for western analysis. Duplicate blots were stained for phosphorylated and nonphosphorylated forms of STAT 1, 3, 5, and 6 by using antibodies specific for each form of the STAT molecule. HELA cells, nonactivated and activated with alpha-interferon were used as positive controls.

These results indicated that under these specific conditions, signaling through MU-1 results in the phosphorylation of STAT 5 at all time points tested (T=0, T=15', T=30', T=60'). Treatment of controls or the chimeric BAF-3 cells with IL-3 resulted in phosphorylation of STAT 3, but not STAT 1 or 5.

Example 4

Tissue Expression of Murine and Human MU-1 Northern Analysis

Northern blots of polyA+ RNA from various tissues (Clontech, Palo Alto, Calif.) were performed as recommended by the manufacturer. For the murine blots, a 262 nucleotide fragment, corresponding to nucleotides 781-1043 of FIG. 1 and SEQ ID NO:9, was used for hybridization.

A single transcript of murine MU-1 was detected in adult murine spleen, lung, and heart tissues. The larger transcript observed in human tissues was not observed in mouse tissues.

Two transcripts of human MU-1 were detected in adult human lymphoid tissues, PBLs, thymus, spleen and lymph node, and in fetal lung.

In Situ Hybridization

In situ hybridization studies were performed by Phylogency Inc. of Columbus, Ohio (according to the method of Lyons et al. (1990) *J. Cell. Biol.* 111:2427-36). Briefly, serial 5-7 micron paraffin sections were deparaffinized, fixed, digested with proteinase K, treated with tri-ethanolamine and dehydrated. cRNAs were prepared from linearized cDNA templates to generate antisense and sense probes. The cRNA transcripts were synthesized according to manufacturer's conditions (Ambion) and labeled with $^{35}$S-UTP. Sections were hybridized overnight, stringently washed and treated with RNase A and dipped in nuclear track emulsion and exposed for 2-3 weeks. Control sections were hybridized with sense probes to indicate the background level of the procedure. The murine probe consisted of an 186 by fragment corresponding to nucleotides 860-1064 (SEQ ID NO:9). The human probe was a 231 by PCR product generated from human MU-1 DNA.

Murine MU-1 expression was observed in the lymph nodes of the adult small intestine at germinal centers and muscularis externa. Specialized lymph nodes and Peyer's patches also exhibited murine MU-1 expression.

Human MU-1 expression was detected at germinal centers of the lymph nodules in the cortex. The medulla, which contains macrophages, was negative for human MU-1. In human spleen, human MU-1 expression was detected in the regions of white pulp but not red pulp.

Example 5

Expression of Human MU-1 in Cells and Cell Lines

RNAse protection analysis was performed on resting and activated human T cells and the B cell lines, Raji and RPMI 8866, and the T cell line Jurkat. Human T cells were activated with anti-CD3 and anti-CD28. The cell lines were activated by phorbol ester and ionomycin. MU-1 riboprobe-producing plasmid was constructed by inserting a 231 by PCR product (PCR was performed by using 5' primer CACAAAGCT-TCAGTATGAGCTGCAGTACAGGAA CCGGGGA (SEQ ID NO: 15) and 3' primer CACAGGATCCCTTTAACT CCTCTGACTGGGTCTGAAAGAT (SEQ ID NO:16)) into the BamH1 and HindIII sites of pGEM3zf(-) (Promega, Madison, Wis.) vector. To make the riboprobe, the riboprobe-producing plasmid was linearized with HindIII. The resulting DNA was phenol/chloroform extracted and precipitated with ethanol. T7 RNA polymerase was used to make the riboprobe according to the protocol suggested by the vendor (PharMingen, San Diego, Calif.). The RNAse protection assay was performed by using PharMingen's RiboQuant Multi-Probe Ribonuclease Protection Assay system. 2.0 ug of total RNA were included in each RPA reaction; after RNAse digestion, the protected riboprobes were run on a QuickPoint rapid nucleic acid separation system (Novex, San Diego, Calif.). Gels were dried and exposed according to the suggestion of the vendor.

Human MU-1 RNA is upregulated in anti-CD3+ anti-CD28-stimulated human purified CD3+ cells when compared with unstimulated populations. MU-1 is also upregulated upon restimulation in Th and Th2-skewed T cell populations. The B cell lines, RPMI 8866 and Raji, constitutively express MU-1 while the Jurkat T cell line does not.

Example 6

Binding of Human MU-1 to Known Cytokines

Both human and murine Ig fusion proteins were constructed and immobilized on Biacore chips in an effort to identify the ligand for MU-1. A variety of cell culture-conditioned media as well as a panel of known cytokines was evaluated for binding to MU-1. Some cytokines were also tested in combination with other receptor chains in the family to consider the possibility that MU-1 may require a second receptor chain for ligand binding. The following cytokines were tested and found to be negative for MU-1 binding: mIL-2, hIL-2, hIL-15, mIL-7, TSLP, TSLP+IL-7, TSLP+IL-7R, TSLP+IL-7g, TSLP+IL-2, TSLP+IL-2+IL-2Rbeta, IL-2Rbeta, IL-2Rgamma, IL-7R, IL-2+2Rbeta, IL-2+2Rgamma, IL-15+IL-2Rbeta, IL-15+2Rgamma, IL-7+2Rgamma, IL-2+IL-7R, IL-15+IL-7R, IL-7+IL-7R. Known receptors have been immobilized as well and tested for MUFc binding with negative results. IL-15 will bind to IL-2Rb but not IL-2Rg or MUFc.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An antibody or fragment thereof that binds to a protein consisting of an amino acid sequence selected from the group consisting of:
 (a) the amino acid sequence of SEQ ID NO:2;
 (b) the amino acid sequence of SEQ ID NO:2 from amino acid 22 to 538;
 (c) the amino acid sequence of SEQ ID NO:2 from amino acid 20 to 538;
 (d) the amino acid sequence of SEQ ID NO:2 from amino acid 22 to 232;
 (e) the amino acid sequence of SEQ ID NO:2 from amino acid 22 to 233;
 (f) the amino acid sequence of SEQ ID NO:2 from amino acid 22 to 234;
 (g) the amino acid sequence of SEQ ID NO:2 from amino acid 22 to 235;
 (h) the amino acid sequence of SEQ ID NO:2 from amino acid 22 to 236;
 (i) the amino acid sequence of SEQ ID NO:2 from amino acid 20 to 232;
 (j) the amino acid sequence of SEQ ID NO:2 from amino acid 20 to 233;
 (k) the amino acid sequence of SEQ ID NO:2 from amino acid 20 to 234;
 (l) the amino acid sequence of SEQ ID NO:2 from amino acid 20 to 235;
 (m) the amino acid sequence of SEQ ID NO:2 from amino acid 20 to 236;
 (n) the amino acid sequence of SEQ ID NO:2 from amino acid 1 to 232;
 (o) the amino acid sequence of SEQ ID NO:2 from amino acid 1 to 233;
 (p) the amino acid sequence of SEQ ID NO:2 from amino acid 1 to 234;
 (q) the amino acid sequence of SEQ ID NO:2 from amino acid 1 to 235; and
 (r) the amino acid sequence of SEQ ID NO:2 from amino acid 1 to 236.

2. The antibody or fragment thereof of claim 1, wherein the amino acid sequence is SEQ ID NO:2.

3. The antibody or fragment thereof of claim 1, wherein the amino acid sequence is SEQ ID NO:2 from amino acid 20 to 538.

4. The antibody or fragment thereof of claim 1, wherein the amino acid sequence is SEQ ID NO:2 from amino acid 20 to 235.

5. The antibody or fragment thereof of claim 1, wherein the amino acid sequence is SEQ ID NO:2 from amino acid 20 to 236.

6. The antibody or fragment thereof of claim 1, wherein the amino acid sequence is SEQ ID NO:2 from amino acid 1 to 235.

7. The antibody or fragment thereof of claim 1, wherein the amino acid sequence is SEQ ID NO:2 from amino acid 1 to 236.

8. A composition comprising the antibody or fragment thereof of claim 1.

9. The antibody or fragment thereof of claim 1, wherein the antibody or fragment thereof specifically reacts with the protein.

10. A method of producing an antibody comprising inoculating an animal with a protein consisting of an amino acid sequence selected from the group consisting of:
 (a) the amino acid sequence of SEQ ID NO:2;
 (b) the amino acid sequence of SEQ ID NO:2 from amino acid 22 to 538;
 (c) the amino acid sequence of SEQ ID NO:2 from amino acid 20 to 538;
 (d) the amino acid sequence of SEQ ID NO:2 from amino acid 22 to 232;
 (e) the amino acid sequence of SEQ ID NO:2 from amino acid 22 to 233;
 (f) the amino acid sequence of SEQ ID NO:2 from amino acid 22 to 234;
 (g) the amino acid sequence of SEQ ID NO:2 from amino acid 22 to 235;
 (h) the amino acid sequence of SEQ ID NO:2 from amino acid 22 to 236;
 (i) the amino acid sequence of SEQ ID NO:2 from amino acid 20 to 232;
 (j) the amino acid sequence of SEQ ID NO:2 from amino acid 20 to 233;
 (k) the amino acid sequence of SEQ ID NO:2 from amino acid 20 to 234;
 (l) the amino acid sequence of SEQ ID NO:2 from amino acid 20 to 235;
 (m) the amino acid sequence of SEQ ID NO:2 from amino acid 20 to 236;
 (n) the amino acid sequence of SEQ ID NO:2 from amino acid 1 to 232;
 (o) the amino acid sequence of SEQ ID NO:2 from amino acid 1 to 233;
 (p) the amino acid sequence of SEQ ID NO:2 from amino acid 1 to 234;
 (q) the amino acid sequence of SEQ ID NO:2 from amino acid 1 to 235; and
 (r) the amino acid sequence of SEQ ID NO:2 from amino acid 1 to 236.

11. An antibody or fragment thereof produced by the method of claim 10, wherein the antibody or fragment thereof binds to a polypeptide consisting of the amino acid sequence of SEQ ID NO:2 or a biologically active fragment thereof.

12. The antibody or fragment thereof of claim 11, wherein the antibody or fragment thereof specifically reacts with the polypeptide.

13. The antibody or fragment thereof of claim 1 or 11, wherein the antibody is a monoclonal antibody.

* * * * *

```
                        SEQUENCE LISTING

<160> NUMBER OF SEQ ID NOS: 19

<210> SEQ ID NO 1
<211> LENGTH: 2665
<212> TYPE: DNA
<213> ORGANISM: homo sapiens
<220> FEATURE:
<221> NAME/KEY: CDS
<222> LOCATION: (236)..(1852)

<400> SEQUENCE: 1
gtcgactgga ggcccagctg cccgtcatca gagtgacagg tcttatgaca gcctgattgg     60
tgactcgggc tgggtgtgga ttctcacccc aggcctctgc ctgctttctc agaccctcat    120
ctgtcacccc cacgctgaac ccagctgcca ccccagaag cccatcagac tgcccccagc     180
acacggaatg gatttctgag aaagaagccg aaacagaagg cccgtgggag tcagc atg     238
                                                                Met
                                                                 1 ccg cgt ggc tgg gcc gcc ccc ttg ctc ctg ctg ctg ctc cag gga ggc     286
Pro Arg Gly Trp Ala Ala Pro Leu Leu Leu Leu Leu Leu Gln Gly Gly
          5                  10                  15 tgg ggc tgc ccc gac ctc gtc tgc tac acc gat tac ctc cag acg gtc     334
Trp Gly Cys Pro Asp Leu Val Cys Tyr Thr Asp Tyr Leu Gln Thr Val
         20                  25                  30 atc tgc atc ctg gaa atg tgg aac ctc cac ccc agc acg ctc acc ctt     382
Ile Cys Ile Leu Glu Met Trp Asn Leu His Pro Ser Thr Leu Thr Leu
 35                  40                  45 acc tgg caa gac cag tat gaa gag ctg aag gac gag gcc acc tcc tgc     430
Thr Trp Gln Asp Gln Tyr Glu Glu Leu Lys Asp Glu Ala Thr Ser Cys
 50                  55                  60                  65 agc ctc cac agg tcg gcc cac aat gcc acg cat gcc acc tac acc tgc     478
Ser Leu His Arg Ser Ala His Asn Ala Thr His Ala Thr Tyr Thr Cys
             70                  75                  80 cac atg gat gta ttc cac ttc atg gcc gac gac att ttc agt gtc aac     526
His Met Asp Val Phe His Phe Met Ala Asp Asp Ile Phe Ser Val Asn
         85                  90                  95 atc aca gac cag tct ggc aac tac tcc cag gag tgt ggc agc ttt ctc     574
Ile Thr Asp Gln Ser Gly Asn Tyr Ser Gln Glu Cys Gly Ser Phe Leu
        100                 105                 110 ctg gct gag agc atc aag ccg gct ccc cct ttc aac gtg act gtg acc     622
Leu Ala Glu Ser Ile Lys Pro Ala Pro Pro Phe Asn Val Thr Val Thr
    115                 120                 125 ttc tca gga cag tat aat atc tcc tgg cgc tca gat tac gaa gac cct     670
Phe Ser Gly Gln Tyr Asn Ile Ser Trp Arg Ser Asp Tyr Glu Asp Pro
130                 135                 140                 145 gcc ttc tac atg ctg aag ggc aag ctt cag tat gag ctg cag tac agg     718
```

```
            Ala Phe Tyr Met Leu Lys Gly Lys Leu Gln Tyr Glu Leu Gln Tyr Arg
                            150                 155                 160 aac cgg gga gac ccc tgg gct gtg agt ccg agg aga aag ctg atc tca        766
Asn Arg Gly Asp Pro Trp Ala Val Ser Pro Arg Arg Lys Leu Ile Ser
            165                 170                 175 gtg gac tca aga agt gtc tcc ctc ctc ccc ctg gag ttc cgc aaa gac        814
Val Asp Ser Arg Ser Val Ser Leu Leu Pro Leu Glu Phe Arg Lys Asp
            180                 185                 190 tcg agc tat gag ctg cag gtg cgg gca ggg ccc atg cct ggc tcc tcc        862
Ser Ser Tyr Glu Leu Gln Val Arg Ala Gly Pro Met Pro Gly Ser Ser
        195                 200                 205 tac cag ggg acc tgg agt gaa tgg agt gac ccg gtc atc ttt cag acc        910
Tyr Gln Gly Thr Trp Ser Glu Trp Ser Asp Pro Val Ile Phe Gln Thr
210                 215                 220                 225 cag tca gag gag tta aag gaa ggc tgg aac cct cac ctg ctg ctt ctc        958
Gln Ser Glu Glu Leu Lys Glu Gly Trp Asn Pro His Leu Leu Leu Leu
                    230                 235                 240 ctc ctg ctt gtc ata gtc ttc att cct gcc ttc tgg agc ctg aag acc       1006
Leu Leu Leu Val Ile Val Phe Ile Pro Ala Phe Trp Ser Leu Lys Thr
                245                 250                 255 cat cca ttg tgg agg cta tgg aag aag ata tgg gcc gtc ccc agc cct       1054
His Pro Leu Trp Arg Leu Trp Lys Lys Ile Trp Ala Val Pro Ser Pro
            260                 265                 270 gag cgg ttc ttc atg ccc ctg tac aag ggc tgc agc gga gac ttc aag       1102
Glu Arg Phe Phe Met Pro Leu Tyr Lys Gly Cys Ser Gly Asp Phe Lys
        275                 280                 285 aaa tgg gtg ggt gca ccc ttc act ggc tcc agc ctg gag ctg gga ccc       1150
Lys Trp Val Gly Ala Pro Phe Thr Gly Ser Ser Leu Glu Leu Gly Pro
290                 295                 300                 305 tgg agc cca gag gtg ccc tcc acc ctg gag gtg tac agc tgc cac cca       1198
Trp Ser Pro Glu Val Pro Ser Thr Leu Glu Val Tyr Ser Cys His Pro
                    310                 315                 320 cca cgg agc ccg gcc aag agg ctg cag ctc acg gag cta caa gaa cca       1246
Pro Arg Ser Pro Ala Lys Arg Leu Gln Leu Thr Glu Leu Gln Glu Pro
                325                 330                 335 gca gag ctg gtg gag tct gac ggt gtg ccc aag ccc agc ttc tgg ccg       1294
Ala Glu Leu Val Glu Ser Asp Gly Val Pro Lys Pro Ser Phe Trp Pro
            340                 345                 350 aca gcc cag aac tcg ggg ggc tca gct tac agt gag gag agg gat cgg       1342
Thr Ala Gln Asn Ser Gly Gly Ser Ala Tyr Ser Glu Glu Arg Asp Arg
        355                 360                 365 cca tac ggc ctg gtg tcc att gac aca gtg act gtg cta gat gca gag       1390
Pro Tyr Gly Leu Val Ser Ile Asp Thr Val Thr Val Leu Asp Ala Glu
370                 375                 380                 385 ggg cca tgc acc tgg ccc tgc agc tgt gag gat gac ggc tac cca gcc       1438
Gly Pro Cys Thr Trp Pro Cys Ser Cys Glu Asp Asp Gly Tyr Pro Ala
                    390                 395                 400 ctg gac ctg gat gct ggc ctg gag ccc agc cca ggc tta gag gac cca       1486
Leu Asp Leu Asp Ala Gly Leu Glu Pro Ser Pro Gly Leu Glu Asp Pro
                405                 410                 415 ctc ttg gat gca ggg acc aca gtc ctg tcc tgt ggc tgt gtc tca gct       1534
Leu Leu Asp Ala Gly Thr Thr Val Leu Ser Cys Gly Cys Val Ser Ala
            420                 425                 430 ggc agc cct ggg cta gga ggg ccc ctg gga agc ctc ctg gac aga cta       1582
Gly Ser Pro Gly Leu Gly Gly Pro Leu Gly Ser Leu Leu Asp Arg Leu
        435                 440                 445 aag cca ccc ctt gca gat ggg gag gac tgg gct ggg gga ctg ccc tgg       1630
Lys Pro Pro Leu Ala Asp Gly Glu Asp Trp Ala Gly Gly Leu Pro Trp
450                 455                 460                 465 ggt ggc cgg tca cct gga ggg gtc tca gag agt gag gcg ggc tca ccc       1678
```

-continued

| | | | | | | | | | | | | |
|---|---|---|---|---|---|---|---|---|---|---|---|---|
|Gly|Gly|Arg|Ser|Pro|Gly|Val|Ser|Glu|Ser|Glu|Ala|Gly|Ser|Pro|
| | | |470| | | |475| | | |480| | |

| ctg | gcc | ggc | ctg | gat | atg | gac | acg | ttt | gac | agt | ggc | ttt | gtg | ggc | tct | 1726 |
|---|---|---|---|---|---|---|---|---|---|---|---|---|---|---|---|---|
| Leu | Ala | Gly | Leu | Asp | Met | Asp | Thr | Phe | Asp | Ser | Gly | Phe | Val | Gly | Ser | |
| | | | 485 | | | | | 490 | | | | | 495 | | | |

| gac | tgc | agc | agc | cct | gtg | gag | tgt | gac | ttc | acc | agc | ccc | ggg | gac | gaa | 1774 |
|---|---|---|---|---|---|---|---|---|---|---|---|---|---|---|---|---|
| Asp | Cys | Ser | Ser | Pro | Val | Glu | Cys | Asp | Phe | Thr | Ser | Pro | Gly | Asp | Glu | |
| | | | 500 | | | | | 505 | | | | | 510 | | | |

| gga | ccc | ccc | cgg | agc | tac | ctc | cgc | cag | tgg | gtg | gtc | att | cct | ccg | cca | 1822 |
|---|---|---|---|---|---|---|---|---|---|---|---|---|---|---|---|---|
| Gly | Pro | Pro | Arg | Ser | Tyr | Leu | Arg | Gln | Trp | Val | Val | Ile | Pro | Pro | Pro | |
| | | | 515 | | | | | 520 | | | | | 525 | | | |

| ctt | tcg | agc | cct | gga | ccc | cag | gcc | agc | taa | tgaggctgac | tggatgtcca | 1872 |
|---|---|---|---|---|---|---|---|---|---|---|---|---|
| Leu | Ser | Ser | Pro | Gly | Pro | Gln | Ala | Ser | | | | |
| 530 | | | | | 535 | | | | | | | | gagctggcca ggccactggg ccctgagcca gagacaaggt cacctgggct gtgatgtgaa   1932
gacacctgca gcctttggtc tcctggatgg gcctttgagc ctgatgttta cagtgtctgt   1992
gtgtgtgtgt gcatatgtgt gtgtgtgcat atgcatgtgt gtgtgtgtgt gtgtcttagg   2052
tgcgcagtgg catgtccacg tgtgtgtgtg attgcacgtg cctgtgggcc tgggataatg   2112
cccatggtac tccatgcatt cacctgccct gtgcatgtct ggactcacgg agctcaccca   2172
tgtgcacaag tgtgcacagt aaacgtgttt gtggtcaaca gatgacaaca gccgtcctcc   2232
ctcctagggt cttgtgttgc aagttggtcc acagcatctc cggggctttg tgggatcagg   2292
gcattgcctg tgactgaggc ggagcccagc cctccagcgt ctgcctccag gagctgcaag   2352
aagtccatat tgttccttat cacctgccaa caggaagcga aaggggatgg agtgagccca   2412
tggtgacctc gggaatggca attttttggg cggcccctgg acgaaggtct gaatcccgac   2472
tctgatacct tctggctgtg ctacctgagc caagtcgcct cccctctctg ggctagagtt   2532
tccttatcca gacagtgggg aaggcatgac acacctgggg gaaattggcg atgtcacccg   2592
tgtacggtac gcagcccaga gcagaccctc aataaacgtc agcttccttc aaaaaaaaaa   2652
aaaaaaatct aga                                                      2665

<210> SEQ ID NO 2
<211> LENGTH: 538
<212> TYPE: PRT
<213> ORGANISM: homo sapiens

<400> SEQUENCE: 2

| | | | | | | | | | | | | | | |
|---|---|---|---|---|---|---|---|---|---|---|---|---|---|---|
|Met|Pro|Arg|Gly|Trp|Ala|Ala|Pro|Leu|Leu|Leu|Leu|Leu|Gln|Gly|
|1| | | |5| | | | |10| | | | |15|

| | | | | | | | | | | | | | | |
|---|---|---|---|---|---|---|---|---|---|---|---|---|---|---|
|Gly|Trp|Gly|Cys|Pro|Asp|Leu|Val|Cys|Tyr|Thr|Asp|Tyr|Leu|Gln|Thr|
| | | |20| | | | |25| | | | |30| | |

| | | | | | | | | | | | | | | |
|---|---|---|---|---|---|---|---|---|---|---|---|---|---|---|
|Val|Ile|Cys|Ile|Leu|Glu|Met|Trp|Asn|Leu|His|Pro|Ser|Thr|Leu|Thr|
| | |35| | | | |40| | | | |45| | | |

| | | | | | | | | | | | | | | |
|---|---|---|---|---|---|---|---|---|---|---|---|---|---|---|
|Leu|Thr|Trp|Gln|Asp|Gln|Tyr|Glu|Glu|Leu|Lys|Asp|Glu|Ala|Thr|Ser|
| |50| | | | |55| | | | |60| | | | |

| | | | | | | | | | | | | | | |
|---|---|---|---|---|---|---|---|---|---|---|---|---|---|---|
|Cys|Ser|Leu|His|Arg|Ser|Ala|His|Asn|Ala|Thr|His|Ala|Thr|Tyr|Thr|
|65| | | | |70| | | | |75| | | | |80|

| | | | | | | | | | | | | | | |
|---|---|---|---|---|---|---|---|---|---|---|---|---|---|---|
|Cys|His|Met|Asp|Val|Phe|His|Phe|Met|Ala|Asp|Ile|Phe|Ser|Val|
| | | | |85| | | | |90| | | | |95| |

| | | | | | | | | | | | | | | |
|---|---|---|---|---|---|---|---|---|---|---|---|---|---|---|
|Asn|Ile|Thr|Asp|Gln|Ser|Gly|Asn|Tyr|Ser|Gln|Glu|Cys|Gly|Ser|Phe|
| | | |100| | | | |105| | | | |110| | |

| | | | | | | | | | | | | | | |
|---|---|---|---|---|---|---|---|---|---|---|---|---|---|---|
|Leu|Leu|Ala|Glu|Ser|Ile|Lys|Pro|Ala|Pro|Pro|Phe|Asn|Val|Thr|Val|
| | |115| | | | |120| | | | |125| | | |

| | | | | | | | | | | | | | | |
|---|---|---|---|---|---|---|---|---|---|---|---|---|---|---|
|Thr|Phe|Ser|Gly|Gln|Tyr|Asn|Ile|Ser|Trp|Arg|Ser|Asp|Tyr|Glu|Asp|

```
                130                 135                 140
Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
        195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Pro His Leu Leu Leu
225                 230                 235                 240

Leu Leu Leu Leu Val Ile Val Phe Ile Pro Ala Phe Trp Ser Leu Lys
                245                 250                 255

Thr His Pro Leu Trp Arg Leu Trp Lys Lys Ile Trp Ala Val Pro Ser
                260                 265                 270

Pro Glu Arg Phe Phe Met Pro Leu Tyr Lys Gly Cys Ser Gly Asp Phe
            275                 280                 285

Lys Lys Trp Val Gly Ala Pro Phe Thr Gly Ser Ser Leu Glu Leu Gly
        290                 295                 300

Pro Trp Ser Pro Glu Val Pro Ser Thr Leu Glu Val Tyr Ser Cys His
305                 310                 315                 320

Pro Pro Arg Ser Pro Ala Lys Arg Leu Gln Leu Thr Glu Leu Gln Glu
                325                 330                 335

Pro Ala Glu Leu Val Glu Ser Asp Gly Val Pro Lys Pro Ser Phe Trp
            340                 345                 350

Pro Thr Ala Gln Asn Ser Gly Gly Ser Ala Tyr Ser Glu Glu Arg Asp
        355                 360                 365

Arg Pro Tyr Gly Leu Val Ser Ile Asp Thr Val Thr Val Leu Asp Ala
    370                 375                 380

Glu Gly Pro Cys Thr Trp Pro Cys Ser Cys Glu Asp Asp Gly Tyr Pro
385                 390                 395                 400

Ala Leu Asp Leu Asp Ala Gly Leu Glu Pro Ser Pro Gly Leu Glu Asp
                405                 410                 415

Pro Leu Leu Asp Ala Gly Thr Thr Val Leu Ser Cys Gly Cys Val Ser
            420                 425                 430

Ala Gly Ser Pro Gly Leu Gly Gly Pro Leu Gly Ser Leu Leu Asp Arg
        435                 440                 445

Leu Lys Pro Pro Leu Ala Asp Gly Glu Asp Trp Ala Gly Gly Leu Pro
    450                 455                 460

Trp Gly Gly Arg Ser Pro Gly Gly Val Ser Glu Ser Glu Ala Gly Ser
465                 470                 475                 480

Pro Leu Ala Gly Leu Asp Met Asp Thr Phe Asp Ser Gly Phe Val Gly
                485                 490                 495

Ser Asp Cys Ser Ser Pro Val Glu Cys Asp Phe Thr Ser Pro Gly Asp
            500                 505                 510

Glu Gly Pro Pro Arg Ser Tyr Leu Arg Gln Trp Val Val Ile Pro Pro
        515                 520                 525

Pro Leu Ser Ser Pro Gly Pro Gln Ala Ser
    530                 535

<210> SEQ ID NO 3
<211> LENGTH: 70
```

```
<212> TYPE: PRT
<213> ORGANISM: homo sapiens

<400> SEQUENCE: 3

Leu Met Thr Asn Ala Phe Ile Ser Ile Ile Asp Asp Leu Ser Lys Tyr
1               5                   10                  15

Asp Val Gln Val Arg Ala Ala Val Ser Ser Met Cys Arg Glu Ala Gly
                20                  25                  30

Leu Trp Ser Glu Trp Ser Gln Pro Ile Tyr Val Gly Asn Asp Glu His
            35                  40                  45

Lys Pro Leu Arg Glu Trp Phe Val Ile Val Ile Met Ala Thr Ile Cys
    50                  55                  60

Phe Ile Leu Leu Ile Leu
65                  70

<210> SEQ ID NO 4
<211> LENGTH: 25
<212> TYPE: DNA
<213> ORGANISM: homo sapiens

<400> SEQUENCE: 4
gagtccgagg agaaagctga tctca                                           25

<210> SEQ ID NO 5
<211> LENGTH: 24
<212> TYPE: DNA
<213> ORGANISM: homo sapiens

<400> SEQUENCE: 5
gaaagatgac cgggtcactc catt                                            24

<210> SEQ ID NO 6
<211> LENGTH: 29
<212> TYPE: DNA
<213> ORGANISM: homo sapiens

<400> SEQUENCE: 6
actcgagcta tgagctgcag gtgcgggca                                       29

<210> SEQ ID NO 7
<211> LENGTH: 29
<212> TYPE: DNA
<213> ORGANISM: homo sapiens

<400> SEQUENCE: 7
actcgagcta tgagctgcag gtgcgggca                                       29

<210> SEQ ID NO 8
<211> LENGTH: 5
<212> TYPE: PRT
<213> ORGANISM: homo sapiens
<220> FEATURE:
<221> NAME/KEY: misc_feature
<222> LOCATION: (3)..(3)
<223> OTHER INFORMATION: Xaa at position 3 may be any amino acid

<400> SEQUENCE: 8

Trp Ser Xaa Trp Ser
1               5

<210> SEQ ID NO 9
<211> LENGTH: 2628
<212> TYPE: DNA
<213> ORGANISM: mus musculus
```

-continued

```
<220> FEATURE:
<221> NAME/KEY: CDS
<222> LOCATION: (407)..(1993)

<400> SEQUENCE: 9
gtcgacgcgg cggtaccagc tgtctgccca cttctcctgt ggtgtgcctc acggtcactt     60
gcttgtctga ccgcaagtct gcccatccct ggggcagcca actggcctca gcccgtgccc    120
caggcgtgcc ctgtctctgt ctggctgccc cagccctact gtcttcctct gtgtaggctc    180
tgcccagatg cccggctggt cctcagcctc aggactatct cagcagtgac tcccctgatt    240
ctggacttgc acctgactga actcctgccc acctcaaacc ttcacctccc accaccacca    300
ctccgagtcc cgctgtgact cccacgccca ggagaccacc caagtgcccc agcctaaaga    360
atggctttct gagaaagacc ctgaaggagt aggtctggga cacagc atg ccc cgg       415
                                                 Met Pro Arg
                                                   1 ggc cca gtg gct gcc tta ctc ctg ctg att ctc cat gga gct tgg agc     463
Gly Pro Val Ala Ala Leu Leu Leu Leu Ile Leu His Gly Ala Trp Ser
  5              10                  15 tgc ctg gac ctc act tgc tac act gac tac ctc tgg acc atc acc tgt     511
Cys Leu Asp Leu Thr Cys Tyr Thr Asp Tyr Leu Trp Thr Ile Thr Cys
 20              25                  30                  35 gtc ctg gag aca cgg agc ccc aac ccc agc ata ctc agt ctc acc tgg     559
Val Leu Glu Thr Arg Ser Pro Asn Pro Ser Ile Leu Ser Leu Thr Trp
             40                  45                  50 caa gat gaa tat gag gaa ctt cag gac caa gag acc ttc tgc agc cta     607
Gln Asp Glu Tyr Glu Glu Leu Gln Asp Gln Glu Thr Phe Cys Ser Leu
         55                  60                  65 cac agg tct ggc cac aac acc aca cat ata tgg tac acg tgc cat atg     655
His Arg Ser Gly His Asn Thr Thr His Ile Trp Tyr Thr Cys His Met
     70                  75                  80 cgc ttg tct caa ttc ctg tcc gat gaa gtt ttc att gtc aat gtg acg     703
Arg Leu Ser Gln Phe Leu Ser Asp Glu Val Phe Ile Val Asn Val Thr
 85                  90                  95 gac cag tct ggc aac aac tcc caa gag tgt ggc agc ttt gtc ctg gct     751
Asp Gln Ser Gly Asn Asn Ser Gln Glu Cys Gly Ser Phe Val Leu Ala
100                 105                 110                 115 gag agc atc aaa cca gct ccc ccc ttg aac gtg act gtg gcc ttc tca     799
Glu Ser Ile Lys Pro Ala Pro Pro Leu Asn Val Thr Val Ala Phe Ser
                120                 125                 130 gga cgc tat gat atc tcc tgg gac tca gct tat gac gaa ccc tcc aac     847
Gly Arg Tyr Asp Ile Ser Trp Asp Ser Ala Tyr Asp Glu Pro Ser Asn
            135                 140                 145 tac gtg ctg agg ggc aag cta caa tat gag ctg cag tat cgg aac ctc     895
Tyr Val Leu Arg Gly Lys Leu Gln Tyr Glu Leu Gln Tyr Arg Asn Leu
        150                 155                 160 aga gac ccc tat gct gtg agg ccg gtg acc aag ctg atc tca gtg gac     943
Arg Asp Pro Tyr Ala Val Arg Pro Val Thr Lys Leu Ile Ser Val Asp
165                 170                 175 tca aga aac gtc tct ctt ctc cct gaa gag ttc cac aaa gat tct agc     991
Ser Arg Asn Val Ser Leu Leu Pro Glu Glu Phe His Lys Asp Ser Ser
180                 185                 190                 195 tac cag ctg cag gtg cgg gca gcg cct cag cca ggc act tca ttc agg    1039
Tyr Gln Leu Gln Val Arg Ala Ala Pro Gln Pro Gly Thr Ser Phe Arg
                200                 205                 210 ggg acc tgg agt gag tgg agt gac ccc gtc atc ttt cag acc cag gct    1087
Gly Thr Trp Ser Glu Trp Ser Asp Pro Val Ile Phe Gln Thr Gln Ala
            215                 220                 225 ggg gag ccc gag gca ggc tgg gac cct cac atg ctg ctc ctg ctg gct    1135
Gly Glu Pro Glu Ala Gly Trp Asp Pro His Met Leu Leu Leu Leu Ala
```

```
                230                 235                  240
gtc ttg atc att gtc ctg gtt ttc atg ggt ctg aag atc cac ctg cct   1183
Val Leu Ile Ile Val Leu Val Phe Met Gly Leu Lys Ile His Leu Pro
    245                 250                 255 tgg agg cta tgg aaa aag ata tgg gca cca gtg ccc acc cct gag agt   1231
Trp Arg Leu Trp Lys Lys Ile Trp Ala Pro Val Pro Thr Pro Glu Ser
260                 265                 270                 275 ttc ttc cag ccc ctg tac agg gag cac agc ggg aac ttc aag aaa tgg   1279
Phe Phe Gln Pro Leu Tyr Arg Glu His Ser Gly Asn Phe Lys Lys Trp
                280                 285                 290 gtt aat acc cct ttc acg gcc tcc agc ata gag ttg gtg cca cag agt   1327
Val Asn Thr Pro Phe Thr Ala Ser Ser Ile Glu Leu Val Pro Gln Ser
        295                 300                 305 tcc aca aca aca tca gcc tta cat ctg tca ttg tat cca gcc aag gag   1375
Ser Thr Thr Thr Ser Ala Leu His Leu Ser Leu Tyr Pro Ala Lys Glu
            310                 315                 320 aag aag ttc ccg ggg ctg ccg ggt ctg gaa gag caa ctg gag tgt gat   1423
Lys Lys Phe Pro Gly Leu Pro Gly Leu Glu Glu Gln Leu Glu Cys Asp
                325                 330                 335 gga atg tct gag cct ggt cac tgg tgc ata atc ccc ttg gca gct ggc   1471
Gly Met Ser Glu Pro Gly His Trp Cys Ile Ile Pro Leu Ala Ala Gly
340                 345                 350                 355 caa gcg gtc tca gcc tac agt gag gag aga gac cgg cca tat ggt ctg   1519
Gln Ala Val Ser Ala Tyr Ser Glu Glu Arg Asp Arg Pro Tyr Gly Leu
                360                 365                 370 gtg tcc att gac aca gtg act gtg gga gat gca gag ggc ctg tgt gtc   1567
Val Ser Ile Asp Thr Val Thr Val Gly Asp Ala Glu Gly Leu Cys Val
        375                 380                 385 tgg ccc tgt agc tgt gag gat gat ggc tat cca gcc atg aac ctg gat   1615
Trp Pro Cys Ser Cys Glu Asp Asp Gly Tyr Pro Ala Met Asn Leu Asp
            390                 395                 400 gct ggc cga gag tct ggc cct aat tca gag gat ctg ctc ttg gtc aca   1663
Ala Gly Arg Glu Ser Gly Pro Asn Ser Glu Asp Leu Leu Leu Val Thr
                405                 410                 415 gac cct gct ttt ctg tct tgc ggc tgt gtc tca ggt agt ggt ctc agg   1711
Asp Pro Ala Phe Leu Ser Cys Gly Cys Val Ser Gly Ser Gly Leu Arg
420                 425                 430                 435 ctt gga ggc tcc cca ggc agc cta ctg gac agg ttg agg ctg tca ttt   1759
Leu Gly Gly Ser Pro Gly Ser Leu Leu Asp Arg Leu Arg Leu Ser Phe
                440                 445                 450 gca aag gaa ggg gac tgg aca gca gac cca acc tgg aga act ggg tcc   1807
Ala Lys Glu Gly Asp Trp Thr Ala Asp Pro Thr Trp Arg Thr Gly Ser
        455                 460                 465 cca gga ggg ggc tct gag agt gaa gca ggt tcc ccc cct ggt ctg gac   1855
Pro Gly Gly Gly Ser Glu Ser Glu Ala Gly Ser Pro Pro Gly Leu Asp
            470                 475                 480 atg gac aca ttt gac agt ggc ttt gca ggt tca gac tgt ggc agc ccc   1903
Met Asp Thr Phe Asp Ser Gly Phe Ala Gly Ser Asp Cys Gly Ser Pro
                485                 490                 495 gtg gag act gat gaa gga ccc cct cga agc tat ctc cgc cag tgg gtg   1951
Val Glu Thr Asp Glu Gly Pro Pro Arg Ser Tyr Leu Arg Gln Trp Val
500                 505                 510                 515 gtc agg acc cct cca cct gtg gac agt gga gcc cag agc agc           1993
Val Arg Thr Pro Pro Pro Val Asp Ser Gly Ala Gln Ser Ser
                520                 525 tagcatataa taaccagcta tagtgagaag aggcctctga gcctggcatt tacagtgtga   2053
acatgtaggg gtgtgtgtgt gtgtgtgtgt gtgtgtgtgt gtgtgtgtgt             2113
gtgtgtgtgt cttgggttgt gtgttagcac atccatgttg ggatttggtc tgttgctatg   2173
```

-continued

```
tattgtaatg ctaaattctc tacccaaagt tctaggccta cgagtgaatt ctcatgttta    2233
caaacttgct gtgtaaacct tgttccttaa tttaatacca ttggttaaat aaaattggct    2293
gcaaccaatt actggaggga ttagaggtag ggggcttttg agttacctgt ttggagatgg    2353
agaaggagag aggagagacc aagaggagaa ggaggaagga gaggagagga gaggagagga    2413
gaggagagga gaggagagga gaggagagga gaggagaggc tgccgtgagg ggagagggac    2473
catgagcctg tggccaggag aaacagcaag tatctggggt acactggtga ggaggtggcc    2533
aggccagcag ttagaagagt agattagggg tgacctccag tatttgtcaa agccaattaa    2593
aataacaaaa aaaaaaaaaa agcggccgct ctaga                               2628

<210> SEQ ID NO 10
<211> LENGTH: 529
<212> TYPE: PRT
<213> ORGANISM: mus musculus

<400> SEQUENCE: 10

Met Pro Arg Gly Pro Val Ala Ala Leu Leu Leu Ile Leu His Gly
 1               5                  10                  15

Ala Trp Ser Cys Leu Asp Leu Thr Cys Tyr Thr Asp Tyr Leu Trp Thr
                20                  25                  30

Ile Thr Cys Val Leu Glu Thr Arg Ser Pro Asn Pro Ser Ile Leu Ser
            35                  40                  45

Leu Thr Trp Gln Asp Glu Tyr Glu Glu Leu Gln Asp Gln Glu Thr Phe
        50                  55                  60

Cys Ser Leu His Arg Ser Gly His Asn Thr Thr His Ile Trp Tyr Thr
 65                  70                  75                  80

Cys His Met Arg Leu Ser Gln Phe Leu Ser Asp Glu Val Phe Ile Val
                85                  90                  95

Asn Val Thr Asp Gln Ser Gly Asn Asn Ser Gln Glu Cys Gly Ser Phe
            100                 105                 110

Val Leu Ala Glu Ser Ile Lys Pro Ala Pro Pro Leu Asn Val Thr Val
        115                 120                 125

Ala Phe Ser Gly Arg Tyr Asp Ile Ser Trp Asp Ser Ala Tyr Asp Glu
    130                 135                 140

Pro Ser Asn Tyr Val Leu Arg Gly Lys Leu Gln Tyr Glu Leu Gln Tyr
145                 150                 155                 160

Arg Asn Leu Arg Asp Pro Tyr Ala Val Arg Pro Val Thr Lys Leu Ile
                165                 170                 175

Ser Val Asp Ser Arg Asn Val Ser Leu Leu Pro Glu Glu Phe His Lys
            180                 185                 190

Asp Ser Ser Tyr Gln Leu Gln Val Arg Ala Ala Pro Gln Pro Gly Thr
        195                 200                 205

Ser Phe Arg Gly Thr Trp Ser Glu Trp Ser Asp Pro Val Ile Phe Gln
    210                 215                 220

Thr Gln Ala Gly Glu Pro Glu Ala Gly Trp Asp Pro His Met Leu Leu
225                 230                 235                 240

Leu Leu Ala Val Leu Ile Ile Val Leu Val Phe Met Gly Leu Lys Ile
                245                 250                 255

His Leu Pro Trp Arg Leu Trp Lys Lys Ile Trp Ala Pro Val Pro Thr
            260                 265                 270

Pro Glu Ser Phe Phe Gln Pro Leu Tyr Arg Glu His Ser Gly Asn Phe
        275                 280                 285

Lys Lys Trp Val Asn Thr Pro Phe Thr Ala Ser Ser Ile Glu Leu Val
    290                 295                 300
```

```
Pro Gln Ser Ser Thr Thr Thr Ser Ala Leu His Leu Ser Leu Tyr Pro
305                 310                 315                 320

Ala Lys Glu Lys Lys Phe Pro Gly Leu Pro Gly Leu Glu Glu Gln Leu
            325                 330                 335

Glu Cys Asp Gly Met Ser Glu Pro Gly His Trp Cys Ile Ile Pro Leu
        340                 345                 350

Ala Ala Gly Gln Ala Val Ser Ala Tyr Ser Glu Glu Arg Asp Arg Pro
            355                 360                 365

Tyr Gly Leu Val Ser Ile Asp Thr Val Thr Val Gly Asp Ala Glu Gly
        370                 375                 380

Leu Cys Val Trp Pro Cys Ser Cys Glu Asp Asp Gly Tyr Pro Ala Met
385                 390                 395                 400

Asn Leu Asp Ala Gly Arg Glu Ser Gly Pro Asn Ser Glu Asp Leu Leu
                405                 410                 415

Leu Val Thr Asp Pro Ala Phe Leu Ser Cys Gly Cys Val Ser Gly Ser
            420                 425                 430

Gly Leu Arg Leu Gly Gly Ser Pro Gly Ser Leu Leu Asp Arg Leu Arg
        435                 440                 445

Leu Ser Phe Ala Lys Glu Gly Asp Trp Thr Ala Asp Pro Thr Trp Arg
450                 455                 460

Thr Gly Ser Pro Gly Gly Gly Ser Glu Ser Glu Ala Gly Ser Pro Pro
465                 470                 475                 480

Gly Leu Asp Met Asp Thr Phe Asp Ser Gly Phe Ala Gly Ser Asp Cys
                485                 490                 495

Gly Ser Pro Val Glu Thr Asp Glu Gly Pro Pro Arg Ser Tyr Leu Arg
            500                 505                 510

Gln Trp Val Val Arg Thr Pro Pro Pro Val Asp Ser Gly Ala Gln Ser
        515                 520                 525

Ser

<210> SEQ ID NO 11
<211> LENGTH: 20
<212> TYPE: DNA
<213> ORGANISM: homo sapiens

<400> SEQUENCE: 11
agcatcaagc cggctccccc                                              20

<210> SEQ ID NO 12
<211> LENGTH: 20
<212> TYPE: DNA
<213> ORGANISM: homo sapiens

<400> SEQUENCE: 12
ctccattcac tccaggtccc                                              20

<210> SEQ ID NO 13
<211> LENGTH: 20
<212> TYPE: DNA
<213> ORGANISM: mus musculus

<400> SEQUENCE: 13
ttgaacgtga ctgtggcctt                                              20

<210> SEQ ID NO 14
<211> LENGTH: 20
<212> TYPE: DNA
<213> ORGANISM: mus musculus
```

<400> SEQUENCE: 14
tgaatgaagt gcctggctga                                               20

<210> SEQ ID NO 15
<211> LENGTH: 40
<212> TYPE: DNA
<213> ORGANISM: homo sapiens

<400> SEQUENCE: 15
cacaaagctt cagtatgagc tgcagtacag gaaccgggga                         40

<210> SEQ ID NO 16
<211> LENGTH: 40
<212> TYPE: DNA
<213> ORGANISM: homo sapiens

<400> SEQUENCE: 16
cacaggatcc ctttaactcc tctgactggg tctgaaagat                         40

<210> SEQ ID NO 17
<211> LENGTH: 551
<212> TYPE: PRT
<213> ORGANISM: Homo sapiens

<400> SEQUENCE: 17

```
Met Ala Ala Pro Ala Leu Ser Trp Arg Leu Pro Leu Leu Ile Leu Leu
1               5                   10                  15

Leu Pro Leu Ala Thr Ser Trp Ala Ser Ala Ala Val Asn Gly Thr Ser
            20                  25                  30

Gln Phe Thr Cys Phe Tyr Asn Ser Arg Ala Asn Ile Ser Cys Val Trp
        35                  40                  45

Ser Gln Asp Gly Ala Leu Gln Asp Thr Ser Cys Gln Val His Ala Trp
    50                  55                  60

Pro Asp Arg Arg Arg Trp Asn Gln Thr Cys Glu Leu Leu Pro Val Ser
65                  70                  75                  80

Gln Ala Ser Trp Ala Cys Asn Leu Ile Leu Gly Ala Pro Asp Ser Gln
                85                  90                  95

Lys Leu Thr Thr Val Asp Ile Val Thr Leu Arg Val Leu Cys Arg Glu
            100                 105                 110

Gly Val Arg Trp Arg Val Met Ala Ile Gln Asp Phe Lys Pro Phe Glu
        115                 120                 125

Asn Leu Arg Leu Met Ala Pro Ile Ser Leu Gln Val Val His Val Glu
    130                 135                 140

Thr His Arg Cys Asn Ile Ser Trp Glu Ile Ser Gln Ala Ser His Tyr
145                 150                 155                 160

Phe Glu Arg His Leu Glu Phe Glu Ala Arg Thr Leu Ser Pro Gly His
                165                 170                 175

Thr Trp Glu Glu Ala Pro Leu Leu Thr Leu Lys Gln Lys Gln Glu Trp
            180                 185                 190

Ile Cys Leu Glu Thr Leu Thr Pro Asp Thr Gln Tyr Glu Phe Gln Val
        195                 200                 205

Arg Val Lys Pro Leu Gln Gly Glu Phe Thr Thr Trp Ser Pro Trp Ser
    210                 215                 220

Gln Pro Leu Ala Phe Arg Thr Lys Pro Ala Ala Leu Gly Lys Asp Thr
225                 230                 235                 240

Ile Pro Trp Leu Gly His Leu Leu Val Gly Leu Ser Gly Ala Phe Gly
                245                 250                 255
```

```
Phe Ile Ile Leu Val Tyr Leu Leu Ile Asn Cys Arg Asn Thr Gly Pro
            260                 265                 270

Trp Leu Lys Lys Val Leu Lys Cys Asn Thr Pro Asp Pro Ser Lys Phe
            275                 280                 285

Phe Ser Gln Leu Ser Ser Glu His Gly Gly Asp Val Gln Lys Trp Leu
            290                 295                 300

Ser Ser Pro Phe Pro Ser Ser Ser Phe Ser Pro Gly Gly Leu Ala Pro
305                 310                 315                 320

Glu Ile Ser Pro Leu Glu Val Leu Glu Arg Asp Lys Val Thr Gln Leu
                325                 330                 335

Leu Leu Gln Gln Asp Lys Val Pro Glu Pro Ala Ser Leu Ser Ser Asn
                340                 345                 350

His Ser Leu Thr Ser Cys Phe Thr Asn Gln Gly Tyr Phe Phe Phe His
            355                 360                 365

Leu Pro Asp Ala Leu Glu Ile Glu Ala Cys Gln Val Tyr Phe Thr Tyr
            370                 375                 380

Asp Pro Tyr Ser Glu Glu Asp Pro Asp Glu Gly Val Ala Gly Ala Pro
385                 390                 395                 400

Thr Gly Ser Ser Pro Gln Pro Leu Gln Pro Leu Ser Gly Glu Asp Asp
                405                 410                 415

Ala Tyr Cys Thr Phe Pro Ser Arg Asp Asp Leu Leu Leu Phe Ser Pro
            420                 425                 430

Ser Leu Leu Gly Gly Pro Ser Pro Ser Thr Ala Pro Gly Gly Ser
            435                 440                 445

Gly Ala Gly Glu Glu Arg Met Pro Pro Ser Leu Gln Glu Arg Val Pro
            450                 455                 460

Arg Asp Trp Asp Pro Gln Pro Leu Gly Pro Pro Thr Pro Gly Val Pro
465                 470                 475                 480

Asp Leu Val Asp Phe Gln Pro Pro Pro Glu Leu Val Leu Arg Glu Ala
                485                 490                 495

Gly Glu Glu Val Pro Asp Ala Gly Pro Arg Glu Gly Val Ser Phe Pro
            500                 505                 510

Trp Ser Arg Pro Pro Gly Gln Gly Glu Phe Arg Ala Leu Asn Ala Arg
            515                 520                 525

Leu Pro Leu Asn Thr Asp Ala Tyr Leu Ser Leu Gln Glu Leu Gln Gly
            530                 535                 540

Gln Asp Pro Thr His Leu Val
545                 550

<210> SEQ ID NO 18
<211> LENGTH: 7
<212> TYPE: PRT
<213> ORGANISM: Mus musculus
<220> FEATURE:
<221> NAME/KEY: SITE
<222> LOCATION: (1)..(7)
<223> OTHER INFORMATION: potential STAT3 binding site

<400> SEQUENCE: 18

Glu Asp Asp Gly Tyr Pro Ala
1               5

<210> SEQ ID NO 19
<211> LENGTH: 4
<212> TYPE: PRT
<213> ORGANISM: Mus musculus
<220> FEATURE:
<221> NAME/KEY: SITE
```

```
<222> LOCATION: (1)..(4)
<223> OTHER INFORMATION: Potential STAT5 binding site

<400> SEQUENCE: 19

Tyr Leu Gln Arg
1
```